US011587681B2

(12) United States Patent
McRaith et al.

(10) Patent No.: US 11,587,681 B2
(45) Date of Patent: *Feb. 21, 2023

(54) DATABASE MANAGEMENT AND GRAPHICAL USER INTERFACES FOR MEASUREMENTS COLLECTED BY ANALYZING BLOOD

(71) Applicant: Welldoc, Inc., Columbia, MD (US)

(72) Inventors: Kevin McRaith, Nonth Potomac, MD (US); Hari Kesani, Columbia, MD (US); Anand Iyer, Potomac, MD (US); Gabriel Susai, Ellicott City, MD (US); Mansur Shomali, Ellicott City, MD (US); Prasad Matti Rao, Ellicott City, MD (US)

(73) Assignee: Welldoc, Inc., Columbia, MD (US)

( * ) Notice: Subject to any disclaimer, the term of this patent is extended or adjusted under 35 U.S.C. 154(b) by 69 days.

This patent is subject to a terminal disclaimer.

(21) Appl. No.: 17/192,433

(22) Filed: Mar. 4, 2021

(65) Prior Publication Data

US 2021/0249133 A1 Aug. 12, 2021

Related U.S. Application Data

(63) Continuation of application No. 17/074,165, filed on Oct. 19, 2020, now Pat. No. 10,978,207, which is a
(Continued)

(51) Int. Cl.
*G16H 50/20* (2018.01)
*G06N 20/00* (2019.01)
(Continued)

(52) U.S. Cl.
CPC ......... *G16H 50/20* (2018.01); *A61B 5/14503* (2013.01); *A61B 5/14532* (2013.01);
(Continued)

(58) Field of Classification Search
CPC ........ G16H 50/20; G16H 10/20; G16H 10/60; G16H 20/00; G16H 20/10; G16H 20/60;
(Continued)

(56) References Cited

U.S. PATENT DOCUMENTS 8,838,513 B2 9/2014 Sudharsan
9,061,153 B1 6/2015 Lebovitz et al.
(Continued)

FOREIGN PATENT DOCUMENTS

WO 2013022775 A1 2/2013
WO WO-2013022775 A1 * 2/2013 ............. G16H 50/70

OTHER PUBLICATIONS

Klaus Donsa et al., "Towards Personalization of Diabetes Therapy Using Computerized Decision Support and Machine Learning: Some Open Problems and Challenges", Jan. 2015, Springer International Publishing, vol. 8700, p. 237-260. (Year: 2015).*
(Continued)

*Primary Examiner* — Rachelle L Reichert
*Assistant Examiner* — Amanda R. Covington
(74) *Attorney, Agent, or Firm* — Bookoff McAndrews, PLLC

(57) ABSTRACT

Methods and devices include database management and graphical user interfaces for measurements collected by analyzing blood.

20 Claims, 12 Drawing Sheets

Related U.S. Application Data continuation of application No. 16/922,744, filed on Jul. 7, 2020, now Pat. No. 10,854,337, which is a continuation of application No. 15/594,237, filed on May 12, 2017, now Pat. No. 10,748,658.

(60) Provisional application No. 62/477,307, filed on Mar. 27, 2017, provisional application No. 62/477,204, filed on Mar. 27, 2017, provisional application No. 62/436,216, filed on Dec. 19, 2016, provisional application No. 62/336,201, filed on May 13, 2016.

(51) Int. Cl.
| | |
|---|---|
| *G16H 10/60* | (2018.01) |
| *G16H 20/00* | (2018.01) |
| *G16H 40/67* | (2018.01) |
| *G16H 20/10* | (2018.01) |
| *G16H 20/60* | (2018.01) |
| *G16H 10/20* | (2018.01) |
| *A61B 5/145* | (2006.01) |

(52) U.S. Cl.
CPC .............. *G06N 20/00* (2019.01); *G16H 10/20* (2018.01); *G16H 10/60* (2018.01); *G16H 20/00* (2018.01); *G16H 20/10* (2018.01); *G16H 20/60* (2018.01); *G16H 40/67* (2018.01)

(58) Field of Classification Search
CPC ................ G16H 40/67; A61B 5/14503; A61B 5/14532; G06N 20/00
See application file for complete search history.

(56) References Cited

U.S. PATENT DOCUMENTS

| | | | |
|---|---|---|---|
| 9,064,040 B2 | 6/2015 | Sudharsan | |
| 2003/0208113 A1 | 11/2003 | Mault et al. | |
| 2003/0208409 A1* | 11/2003 | Mault | G06F 19/3475 705/15 |
| 2008/0201174 A1 | 8/2008 | Ramasubramanian et al. | |
| 2008/0234992 A1* | 9/2008 | Ray | G01N 33/66 703/2 |
| 2008/0268412 A1* | 10/2008 | Mulcahy | G16H 20/60 434/262 |
| 2009/0234916 A1* | 9/2009 | Cosentino | G16H 10/60 709/203 |
| 2010/0305965 A1* | 12/2010 | Benjamin | G06Q 50/22 705/2 |
| 2012/0179484 A1* | 7/2012 | Urdea | G01N 33/48714 705/2 |
| 2012/0246102 A1 | 9/2012 | Sudharsan | |
| 2013/0226608 A1 | 8/2013 | Lascia et al. | |
| 2013/0317316 A1* | 11/2013 | Kandeel | G16H 15/00 600/300 |
| 2014/0155705 A1 | 6/2014 | Papadopoulos et al. | |
| 2014/0176134 A1* | 6/2014 | Newman | A61B 3/0058 324/309 |
| 2014/0207486 A1 | 7/2014 | Carty et al. | |
| 2014/0249851 A1 | 9/2014 | Christodouleas et al. | |
| 2014/0288680 A1* | 9/2014 | Hoffman | G06K 9/00342 700/91 |
| 2014/0324445 A1* | 10/2014 | Carlsgaard | G06Q 10/10 705/2 |
| 2014/0358581 A1 | 12/2014 | Sudharsan | |
| 2015/0006192 A1* | 1/2015 | Sudharsan | G06N 5/048 705/2 |
| 2015/0006456 A1 | 1/2015 | Sudharsan | |
| 2015/0006462 A1 | 1/2015 | Sudharsan | |
| 2015/0081209 A1* | 3/2015 | Yeh | G06F 16/60 701/427 |
| 2015/0105631 A1* | 4/2015 | Tran | A61B 5/0024 600/301 |
| 2015/0248533 A1 | 9/2015 | Sudharsan | |
| 2017/0220751 A1* | 8/2017 | Davis | A61B 5/0015 |
| 2017/0351842 A1* | 12/2017 | Booth | G16H 40/63 |

OTHER PUBLICATIONS

An intelligent medication system designed to improve the medication adherence Marios A. S. Rodrigues; Vandermi J. Silva; Vicente F. de Lucena Consumer Electronics—Berlin (ICCE-Berlin), 2015 IEEE 5th International Conference on Year: 2015 pp. 46-19, DOI: 10.1109/ICCE-Berlin.2015.7391310 IEEE Conference Publications.

Improving quality of life of elderly people aged 85 and older by improving treatment adherence Ioana Dana Alexa; Gabriel loan Prada; Valer Ioan Donca; Liana Mioara Mos; Ovidiu Alexa E-Health and Bioengineering Conference (EHB), 2013 Year: 2013 pp. 1-4, DOI: 10.1109/EHB.2013.6707380 IEEE Conference Publications.

Medication adherence system using SMS technology I. Sachpazidis; S. Fragou; G. Sakas Intelligent Sensors, Sensor Networks and Information Processing Conference, 2004. Proceedings of the 2004 Year: 2004 pp. 571-575, DOI: 10.1109/ISSNIP.2004.1417524 IEEE Conference Publications.

Medication adherence using a smart pill bottle Dana DeMeo; Michael Morena Emerging Technologies for a Smarter World (CEWIT), 2014 11th International Conference & Expo on Year: 2014 pp. 1-4, DOI: 10.1109/CEWIT.2014.7021149 IEEE Conference Publications.

Klaus Donsa et al., Towards Personalization of Diabetes Therapy Using Computerized Decision Support and Machine Learning: Some Open Problems and Challenges, Network and Parallel Computing, Jan. 1, 2015, pp. 237-260.

Catherine Mcnamara et al., Algorithms to optimise the medication for patients with Diabetes Type 2 and Guidelines for Referral to Secondary Services for Waitemata General Practitioners, Retrieved from the Internet: http://www.waitematadhb.govt.nz/assets/Documents/health-professionals/medicines/Diabetes-Algorithms-v0-0-1.pdf, Aug. 26, 2010, 14 pages.

Anonymous, Diabetes management, Wikipedia, Retrieved from the Internet: https://en.wikipedia.org/w/index.php?title=Diabetes_management&oldid=715994640, Apr. 19, 2016, 24 pages.

Alison Gray, Nutritional Recommendations for Individuals with Diabetes, NCBI Bookshelf, Retrieved from the Internet: https://www.ncbi.nlm.nih.gov/books/NBK279012, May 31, 2015, 32 pages.

International Search Report and Written Opinion dated Aug. 10, 2017, in PCT Application No. PCT/US2017/032515 (17 pages).

* cited by examiner

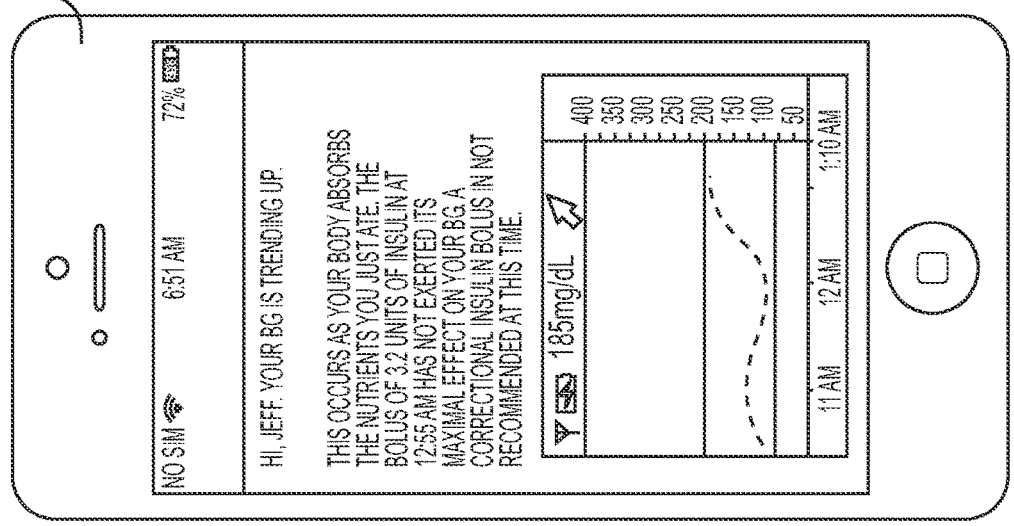
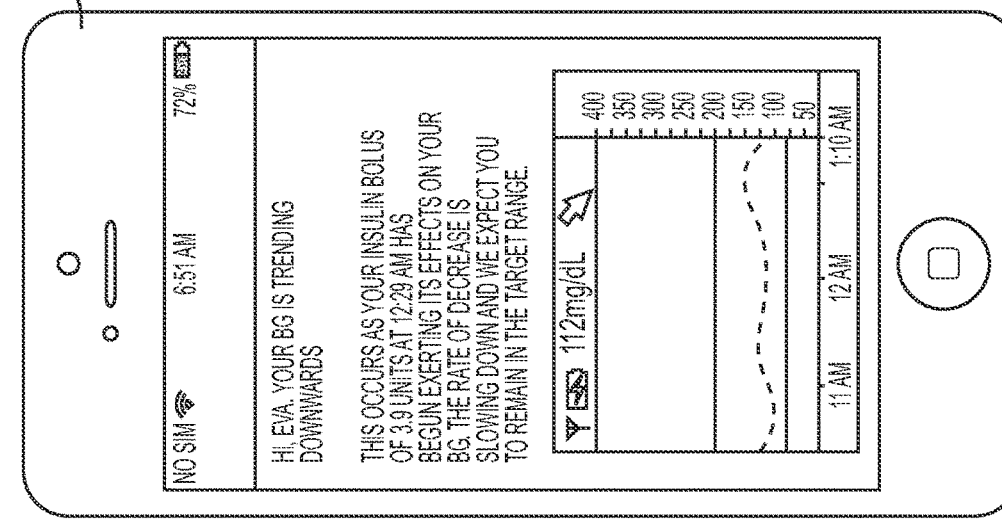
FIG. 11

DATABASE MANAGEMENT AND GRAPHICAL USER INTERFACES FOR MEASUREMENTS COLLECTED BY ANALYZING BLOOD

CROSS-REFERENCE TO RELATED APPLICATIONS

This application is a continuation of and claims the benefit of priority to U.S. application Ser. No. 17/074,165, filed Oct. 19, 2020, which is a continuation of U.S. application Ser. No. 16/922,744, filed Jul. 7, 2020, now U.S. Pat. No. 10,854,337, which is a continuation of U.S. application Ser. No. 15/594,237, filed May 12, 2017, now U.S. Pat. No. 10,748,658, issued Aug. 18, 2020, which claims the benefit of U.S. Provisional Application No. 62/336,201, filed May 13, 2016; U.S. Provisional Application No. 62/436,216, filed Dec. 19, 2016; U.S. Provisional Application No. 62/477,204, filed Mar. 27, 2017; and U.S. Provisional Application No. 62/477,307, filed Mar. 27, 2017, the entireties of each of which are incorporated by reference herein.

TECHNICAL FIELD

The present disclosure relates generally to obtaining and processing data to generate treatment plans and clinical recommendations for managing the health of a user, and, in some embodiments, specifically toward plans and recommendations for managing blood glucose levels of a user via a mobile application.

INTRODUCTION

Increased healthcare costs have limited patient access to appropriate care. At the same time, healthcare companies have increased provider workloads and limited physician-patient interactions. Physicians often ascertain patient compliance with treatment instructions after subsequent patient visits and evaluation. In some cases, failure to comply with physician treatment instructions may lead to prolonged patient illness and/or worsened patient health. This in turn may lead to improper patient assessments and treatment. Moreover, patient compliance with a physician's treatment instructions may still fail to provide patients with dynamic healthcare information and assistance with managing their disease.

In some cases, failure to comply with physician treatment instructions may lead to improper dosage of medication. Often, specific doses of insulin that a given patient requires is unknown, and physicians or nurses may need to change the dose iteratively until the desired dosage is achieved. This process, known as titration, can be driven by a physician, nurse or other health care provider. Self-titration (by a patient who is given an algorithm from the provider) has been well validated, however, patients often need support in following self-titration algorithms.

SUMMARY

This disclosure is directed to a computer-implemented method for managing blood glucose levels of a user, the method comprises electronically receiving, by one or more processors and before generation of a treatment plan, initial data including a length of time that the user has been diagnosed with a blood glucose condition, determining a goal for the user to achieve over a treatment period based on the initial data, generating a treatment plan for the user to achieve the goal based on the length of time that the user has been diagnosed with the blood glucose condition, presenting the treatment plan to the user via an electronic device of the user, electronically receiving, by the one or more processors, data relating to the treatment plan during a first subset of the treatment period, analyzing, using a machine learning algorithm, the data to identify patterns between different subsets of the data, revising the goal and the treatment plan for a subsequent subset of the treatment period based on the identified patterns, and presenting the revised treatment plan to the user via the electronic device.

The initial data also includes types and dosages of medications consumed by the user and historical A1C values of the user. The goal includes a reduction in the A1C value of the user at an end of a treatment period, as compared to an A1C value of the user at a beginning of the treatment period. The treatment plan includes instructions for tasks to be performed by the user during the first subset of the treatment period, wherein the tasks include one or more prescribed blood glucose measurement pairs to be measured before and after meals, prescribed timing and dosage of medication to be consumed by the user, a prescribed amount of carbohydrates to be consumed by the user, and prescribed exercise for the user to perform. The revised treatment plan includes one or more tasks to be performed by the user during the subsequent subset of the treatment period, wherein the tasks include a change in the one or more prescribed blood glucose measurement pairs to be measured before and after meals, prescribed timing and dosage of medication to be consumed by the user, a prescribed amount of carbohydrates for the user to consume, and prescribed exercise for the user to perform, as compared to the first subset of the treatment period. The data relating to the treatment plan includes types, timing, and dosages of medications consumed by the user, times and amounts of carbohydrates consumed by the user, amount of sleep of the user, amount of exercise performed by the user, and blood glucose levels of the user. The also includes receiving GPS data from the electronic device of the user, based on a time proximity to one or more scheduled meals of the treatment plan to be consumed by the user, using the GPS data to identify restaurants in proximity to the user and that are cataloged in a database, wherein the database includes meals offered by the cataloged restaurants and their carbohydrate content, presenting a list of the catalogued restaurants to the user via the electronic device, wherein the list includes recommended meal options at the identified restaurants based on the carbohydrate content of meals offered by the cataloged restaurants, receiving a selection of a catalogued restaurant from the user, and generating a walking route for the user to travel along from a current location of the user to the selected restaurant. The method further includes receiving an indication from the user that the user would like to exercise, and, after receiving the indication from the user, retrieving GPS data from the electronic device of the user, and generating a route for the user to walk along, wherein a distance of the route corresponds to exercise prescribed to the user in the treatment plan. The method further includes administering, via a software application downloaded to the electronic device of the user, a questionnaire to the user, electronically receiving, by one or more processors, user answers to the questionnaire, determining, based on the user answers to the questionnaire, a tendency of the user to follow a medication regimen, a diet regimen, and an exercise regimen, and wherein generating the treatment plan for the user to achieve the goal also is based on the tendency of the user to follow a medication regimen, a diet regimen, and an exercise regimen. The method further includes determining, based on the identified patterns, a trigger event that occurs before an adverse effect on blood glucose levels of the user. The method further includes sending a notification to the user via the electronic device upon detecting a subsequent instance of the trigger event. The notification includes an identification of the trigger event to the user and an identification of the adverse effect on blood glucose that occurs after the trigger event. The trigger event is a day of the week. Another trigger event is an amount of exercise performed by the user that exceeds a threshold. The adverse effect on blood glucose levels includes hyperglycemia.

The disclosure may also be directed to a system for managing blood glucose levels of a user, the system comprising a memory having processor-readable instructions stored therein, and a processor configured to access the memory and execute the processor-readable instructions, which, when executed by the processor configures the processor to perform a method, the method comprising electronically receiving, by one or more processors and before generation of a treatment plan, initial data including a length of time that the user has been diagnosed with a blood glucose condition, determining a goal for the user to achieve over a treatment period based on the initial data, generating a treatment plan for the user to achieve the goal based on the length of time that the user has been diagnosed with the blood glucose condition, presenting the treatment plan to the user via an electronic device of the user, electronically receiving, by the one or more processors, data relating to the treatment plan during a first subset of the treatment period, analyzing, using a machine learning algorithm, the data to identify patterns between different subsets of the data, revising the goal and the treatment plan for a subsequent subset of the treatment period based on the identified patterns, and presenting the revised treatment plan to the user via the electronic device. The initial data also includes types and dosages of medications consumed by the user and historical A1C values of the user. The goal includes a reduction in the A1C value of the user at an end of a treatment period, as compared to an A1C value of the user at a beginning of the treatment period.

The disclosure may also be directed to a computer-implemented method for managing blood glucose levels of a user, the method comprising electronically receiving, by one or more processors and before generation of a treatment plan, data including a length of time that the user has been diagnosed with a blood glucose condition, types and dosages of medications consumed by the user, and A1C values of the user, determining a goal for the user, wherein the goal includes a reduction in the A1C value of the user at an end of a treatment period, as compared to an A1C value of the user at a beginning of the treatment period, generating the treatment plan for the user to achieve the goal based on the length of time that the user has been diagnosed with the blood glucose condition, and the types and dosages of medications consumed by the user, wherein the treatment plan includes instructions for tasks to be performed by the user during a first subset of the treatment period, wherein the tasks include one or more prescribed blood glucose measurement pairs to be measured before and after meals, prescribed timing and dosage of medication to be consumed by the user, a prescribed amount of carbohydrates to be consumed by the user, and prescribed exercise for the user to perform, presenting the treatment plan to the user via an electronic device of the user, electronically receiving, by the one or more processors, data relating to the treatment plan during the first subset of the treatment period, the data including types, timing, and dosages of medications consumed by the user, times and amounts of carbohydrates consumed by the user, amount of sleep of the user, amount of exercise performed by the user, and blood glucose levels of the user, determining a medication compliance by comparing the received types, timing, and dosages of medication to the prescribed types, timing, and dosages of medication, determining a diet compliance by comparing the received amounts of carbohydrates consumed to the prescribed amounts of carbohydrates to be consumed, determining an exercise compliance by comparing the received amounts of exercise performed to the prescribed amounts of exercise to be performed, analyzing, using a machine learning algorithm, the types, timing, and dosages of medications consumed by the user, amounts of carbohydrates consumed by the user, amount of sleep of the user, amount of exercise performed by the user, and blood glucose levels of the user to identify patterns between the types, timing, and dosages of medications consumed by the user, amounts of carbohydrates consumed by the user, amount of sleep of the user, amount of exercise performed by the user, and the blood glucose levels of the user, revising the treatment plan for a subsequent subset of the treatment period based on the determined medication compliance, the determined diet compliance, the determined exercise compliance, and the identified patterns, presenting the revised treatment plan to the user via the electronic device, wherein the revised treatment plan includes one or more tasks to be performed by the user during the subsequent subset of the treatment period, wherein the tasks include a change in the one or more prescribed blood glucose measurement pairs to be measured before and after meals, prescribed timing and dosage of medication to be consumed by the user, a prescribed amount of carbohydrates for the user to consume, and prescribed exercise for the user to perform, as compared to the first subset of the treatment period, receiving GPS data from the electronic device of the user, based on a time proximity to one or more scheduled meals of the treatment plan to be consumed by the user, using the GPS data to identify restaurants in proximity to the user and that are cataloged in a database, wherein the database includes meals offered by the cataloged restaurants and their carbohydrate content, presenting a list of the catalogued restaurants to the user via the electronic device, wherein the list includes recommended meal options at the identified restaurants based on the carbohydrate content of meals offered by the cataloged restaurants, receiving a selection of a catalogued restaurant from the user, generating a walking route for the user to travel along from a current location of the user to the selected restaurant, administering, via a software application downloaded to the electronic device of the user, a questionnaire to the user, electronically receiving, by one or more processors, user answers to the questionnaire, determining, based on the user answers to the questionnaire, a tendency of the user to follow the medication regimen, the diet regimen, and the exercise regimen, and wherein generating the treatment plan for the user to achieve the goal also is based on the tendency of the user to follow a medication regimen, a diet regimen, and an exercise regimen, determining, based on the identified patterns, a trigger event that occurs before an adverse effect on blood glucose levels of the user, sending a notification to the user via the electronic device upon detecting a subsequent instance of the trigger event, wherein the notification includes an identification of the trigger event to the user and an identification of the adverse effect on blood glucose that occurs after the trigger event, the trigger event is a day of the week or is an amount of exercise performed by the user that exceeds a threshold, and the adverse effect on blood glucose levels includes hyperglycemia. The method further includes receiving an indication from the user that the user would like to exercise, and, after receiving the indication from the user, retrieving GPS data from the electronic device of the user, and generating a route for the user to walk along, wherein a distance of the route corresponds to the exercise prescribed to the user in the treatment plan.

BRIEF DESCRIPTION OF THE DRAWINGS

The accompanying drawings, which are incorporated in and constitute a part of this specification, illustrate examples of the disclosure and together with the description, serve to explain the principles of the disclosure.

FIG. 11 is two screenshots of two exemplary messages, in accordance with an example of the present disclosure.

DETAILED DESCRIPTION

Reference will now be made in detail to examples of the disclosure, which are illustrated in the accompanying drawings. Wherever possible, the same reference numbers will be used throughout the drawings to refer to the same or like parts.

In the discussion that follows, relative terms such as "about," "substantially," "approximately," etc. are used to indicate a possible variation of ±10% in a stated numeric value. It should be noted that the description set forth herein is merely illustrative in nature and is not intended to limit the examples of the subject matter, or the application and uses of such examples. Any implementation described herein as exemplary is not to be construed as preferred or advantageous over other implementations. Rather, as alluded to above, the term "exemplary" is used in the sense of example or "illustrative," rather than "ideal." The terms "comprise," "include," "have," "with," and any variations thereof are used synonymously to denote or describe a non-exclusive inclusion. As such, a process, method, article, or apparatus that uses such terms does not include only those steps, structure or elements but may include other steps, structures or elements not expressly listed or inherent to such process, method, article, or apparatus. Further, the terms "first," "second," and the like, herein do not denote any order, quantity, or importance, but rather are used to distinguish one element from another. Moreover, the terms "a" and "an" herein do not denote a limitation of quantity, but rather denote the presence of at least one of the referenced item.

Healthcare and Computing Environment

Figure 1:
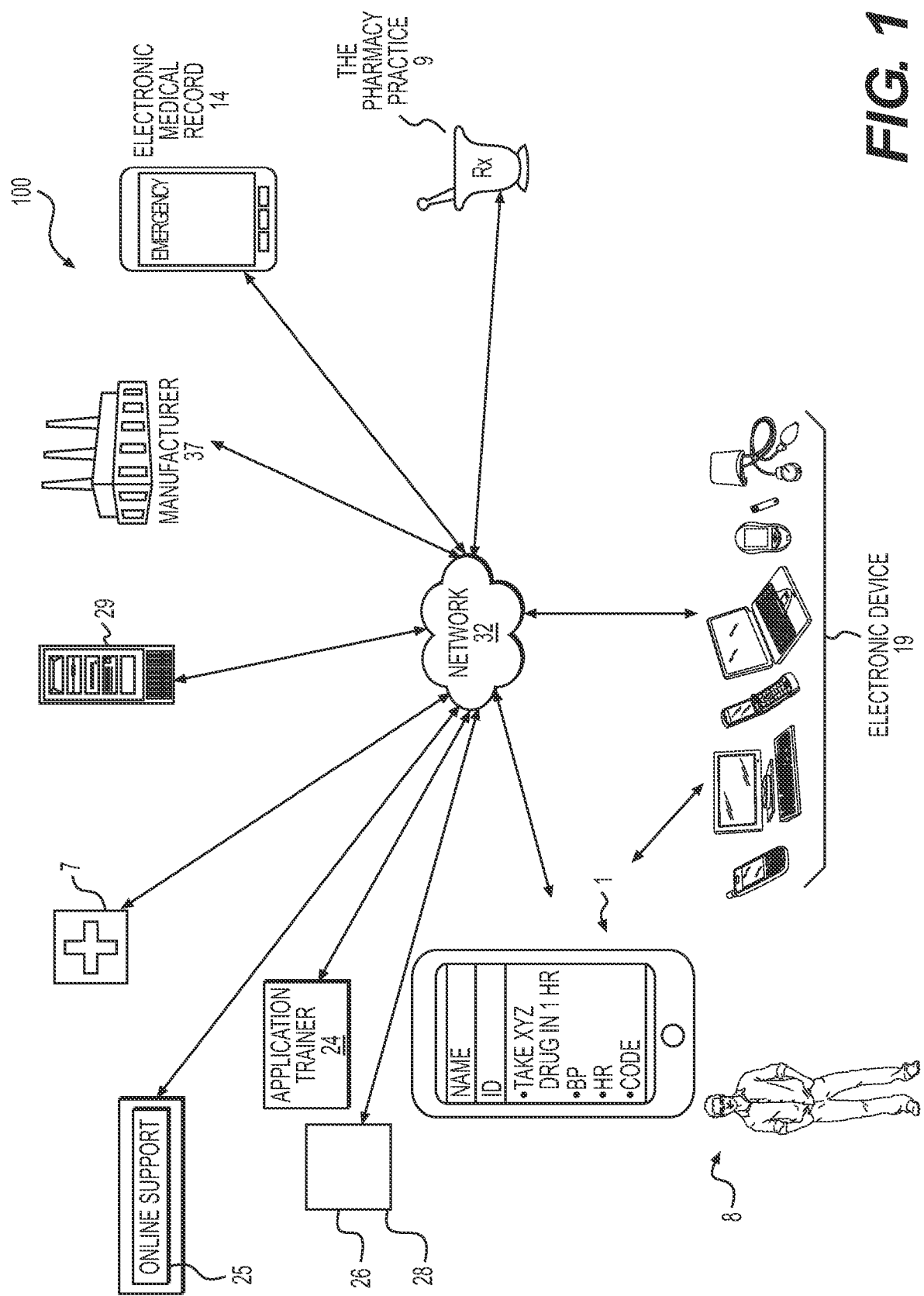
FIG. 1 is a schematic illustration of a health management system, according to an example of the present disclosure.

FIG. 1 is a block diagram of a health management system 100, according to an example of the present disclosure. A user (e.g., a patient, consumer, or the like) 8 having an electronic device 19, such as a mobile device, computer, medical device, or any other electronic device configured to access an electronic network 32, such as the Internet, may communicate with or otherwise access a mobile health (mHealth) application 1. In some examples, network 32 may include wireless or wired links, such as mobile telephone networks, Wi-Fi, LANs, WANs, Bluetooth, near-field communication (NFC), or other suitable forms of network communication. Multiple electronic devices 19 may be configured to access electronic network 32. A user 8 may access mHealth application 1 with a single account linked to multiple electronic devices 19 (e.g., via one or more of a mobile phone, a tablet, and a laptop computer). Electronic device 19 also may include, but is not limited to, mobile health devices, a desktop computer or workstation, a laptop computer, a mobile handset, a personal digital assistant (PDA), a cellular telephone, a network appliance, a camera, a smart phone, a smart watch, an enhanced general packet radio service (EGPRS) mobile phone, a media player, a navigation device, a game console, a set-top box, a biometric sensing device with communication capabilities, a smart TV, or any combination of these or other types of computing devices having at least one processor, a local memory, a display (e.g., a monitor or touchscreen display), one or more user input devices, and a network communication interface. The electronic device 19 may include any type or combination of input/output devices, such as a display monitor, keyboard, touchpad, accelerometer, gyroscope, mouse, touchscreen, camera, a projector, a touch panel, a pointing device, a scrolling device, a button, a switch, a motion sensor, an audio sensor, a pressure sensor, a thermal sensor, and/or microphone. Electronic devices 19 also may communicate with each other by any suitable wired or wireless means (e.g., via Wi-Fi, radio frequency (RF), infrared (IR), Bluetooth, Near Field Communication, or any other suitable means) to send and receive information.

mHealth application 1 may be in communication with other entities or networks to send and receive information. In some examples, mHealth application 1 may communicate with one or more applications associated with the user 8 such as, e.g., exercise tracking (e.g., step tracking) applications and/or other health-related applications. mHealth application 1 may be able to import data from the other applications to analyze and use in generating treatment plans for the user 8. For example, mHealth application 1 may import activity tracking data from another application and use that data to identify patterns between user 8 exercise and blood glucose values collected prior to the use of mHealth application 1. mHealth application 1 also may import any other suitable data from other mobile health applications such as, e.g., blood pressure, BMI, A1C, exercise type, exercise duration, exercise distance, calories burned, total steps, exercise date, exercise start and stop times, and sleep. mHealth application 1 also may export data to other mobile applications, including, e.g., other mobile health applications having social or interactive features. A healthcare provider 7, such as a physician, may prescribe the application. However, it is also contemplated that mHealth application 1 may not require a prescription, e.g., that it may be a commercially available consumer application accessible without a prescription from a digital distribution platform for computer software. mHealth application 1 may be tailored to a specific user 8 and may be activated in person by the user 8 by visiting a pharmacy 9 or other authorized entity. For example, the user 8 may receive an access code from the pharmacy that authorizes access to mHealth application 1. The user 8 may receive training on using mHealth application 1 by a mHealth support system 25 and/or application trainer 24. mHealth application 1 may include programming 28 of various forms, such as machine learning programming algorithms 26. The user treatment plan may include a prescription (e.g., for a drug, device, and/or therapy), which may be dispensed by the pharmacy 9. The pharmacy 9 may allow the refill of the prescribed product/therapy after receiving authorization based on the user's compliance with his/her healthcare treatment plan. The authorization may be received by the pharmacy 9 by a communication from the application 1, via, e.g., the network 32 and various servers 29. Use of the drug or other medical product/therapy also may be sent to the manufacturer 37 over the network 32 to inform the manufacturer 37 of the amount of medical product or therapy being used by user 8. This information may assist the manufacturer 37 in assessing demand and planning supply of the medical product or therapy. The healthcare provider 7 also may receive a report based on the user information received by the application 1, and may update the user treatment plan based on this information. The user's electronic medical record 14 also may be automatically updated via the network 32 based on the user information, which may include electronically transmitted user 8 feedback on the application, received by mHealth application 1. Healthcare provider 7 may be any suitable healthcare provider including, e.g., a doctor, specialist, nurse, educator, social worker, MA, PA, or the like.

Figure 2:
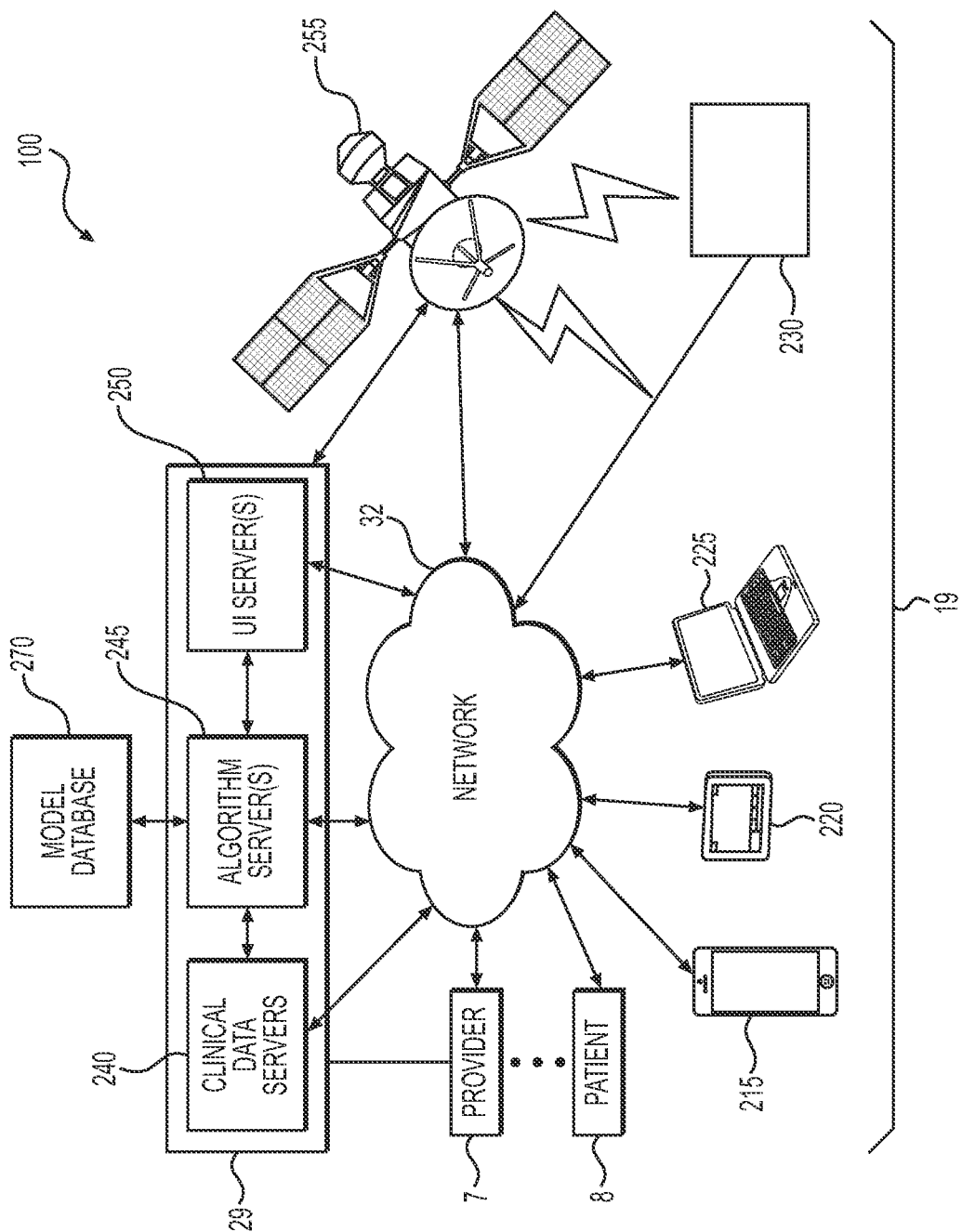
FIG. 2 is a schematic illustration of a portion of the health management system of FIG. 1.

FIG. 2 is a schematic diagram of additional aspects of system 100. For example, the system 100 may access decision models stored on a decision model database 270 via network 32. The retrieved decision models may be used for display and/or processing by one or more electronic devices 19, such as a mobile device 215, a tablet device 220, a computer (e.g., a laptop or desktop) 225, a kiosk 230 (e.g., at a kiosk, pharmacy, clinic, or hospital having medical and/or prescription information), and/or any device connected to network 32.

In the example shown in FIG. 2, mobile device 215, tablet 220, and computer 225 each may be equipped with or include, for example, a GPS receiver for obtaining and reporting location information, e.g., GPS data, via network 32 to and from any of servers 29 and/or one or more GPS satellites 255.

Each of electronic devices 19, including mobile device 215, tablet device 220, computer 225, and/or kiosk 230, may be configured to send and receive data (e.g., clinical information) to and from a system of servers 29 over network 32. Each of devices 19 may receive information, such as clinical data via the network 32 from servers 29. Servers 29 may include clinical data servers 240, algorithm servers 245, user interface (UI) servers 250, and/or any other suitable servers. Electronic device 19 may include a user interface that is in data communication with UI server 250 via network 32. Each server may access the decision model database 270 to retrieve decision models. Each server may include memory, a processor, and/or a database. For example, the clinical data server 240 may have a processor configured to retrieve clinical data from a provider's database and/or a patient's electronic medical record. The algorithm server 245 may have a database that includes various algorithms, and a processor configured to process the clinical data. The UI server 250 may be configured to receive and process user 8 input, such as clinical decision preferences. The satellite 255 may be configured to send and receive information between servers 29 and devices 19.

The clinical data server 240 may receive clinical data, such as data regarding the user from the electronic device 19 via the network 32 or indirectly via the UI server 250. The clinical data server 240 may save the information in memory, such as a computer readable memory.

The clinical data server 240 also may be in communication with one or more other servers, such as the algorithm server 245 and/or external servers. The servers 29 may include data about provider preferences, and/or user 8 health history. In addition, the clinical data server 240 may include data from other users. The algorithm server 245 may include machine learning, and/or other suitable algorithms. The algorithm server 245 also may be in communication with other external servers and may be updated as desired. For example, the algorithm server 245 may be updated with new algorithms, more powerful programming, and/or more data. The clinical data server 240 and/or the algorithm server 245 may process the information and transmit data to the model database 270 for processing. In one example, algorithm server(s) 245 may obtain a pattern definition in a simple format, predict several time steps in the future by using models, e.g., Markov models, Gaussian, Bayesian, and/or classification models such as linear discriminant functions, nonlinear discriminant functions, random forest algorithms and the like, optimize results based on its predictions, detect transition between patterns, obtain abstract data and extract information to infer higher levels of knowledge, combine higher and lower levels of information to understand about the user 8 and clinical behaviors, infer from multi-temporal (e.g., different time scales) data and associated information, use variable order Markov models, and/or reduce noise over time by employing clustering algorithms, such as k-means clustering.

Each server in the system of servers 29, including clinical data server 240, algorithm server 245, and UI server 250, may represent any of various types of servers including, but not limited to, a web server, an application server, a proxy server, a network server, or a server farm. Each server in the system of servers 29 may be implemented using, for example, any general-purpose computer capable of serving data to other computing devices including, but not limited to, devices 19 or any other computing device (not shown) via network 32. Such a general-purpose computer can include, but is not limited to, a server device having a processor and memory for executing and storing instructions. The memory may include any type of random access memory (RAM) or read-only memory (ROM) embodied in a physical storage medium, such as magnetic storage including floppy disk, hard disk, or magnetic tape; semiconductor storage such as solid-state disk (SSD) or flash memory; optical disc storage; or magneto-optical disc storage. Software may include one or more applications and an operating system. Hardware can include, but is not limited to, a processor, memory, and graphical UI display. Each server also may have multiple processors and multiple shared or separate memory components that are configured to function together within, for example, a clustered computing environment or server farm.

Figure 3:
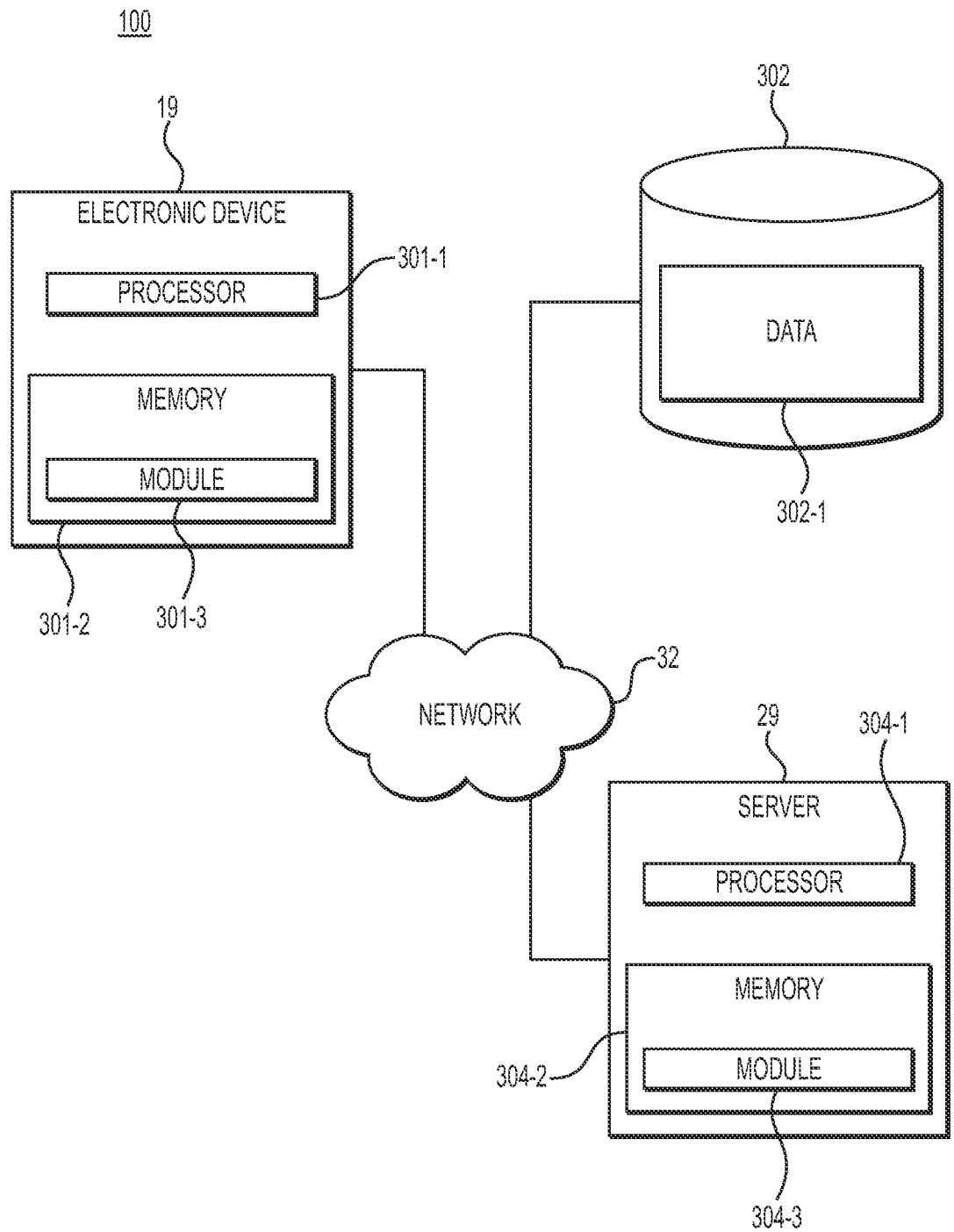
FIG. 3 is a schematic illustration of another portion of the health management system of FIG. 1.

FIG. 3 is another representation of a portion of system 100 showing additional details of electronic device 19 and a server 29. Electronic device 19 and server 29 each may contain one or more processors, such as processors 301-1 and 304-1. Processors 301-1 and 304-1 each may be a central processing unit, a microprocessor, a general purpose processor, an application specific processor, or any device that executes instructions. Electronic device 19 and server 29 also may include one or more memories, such as memories 301-2 and 304-2, that store one or more software modules. Memories 301-2 and 304-2 may be implemented using any computer-readable storage medium, such as hard drives, CDs, DVDs, flash memory, RAM, ROM, etc. Memory 301-2 may store a module 301-3, which may be executed by processor 301-1. Similarly, memory 304-2 may store a module 304-3, which may be executed by processor 304-1.

Electronic device 19 may further comprise one or more UIs. The UI may allow one or more interfaces to present information to a user 8, such as a plan or intervention. The UI may be web based, such as a web page, or a stand-alone application. The UI also may be configured to accept information about a user 8, such as data inputs and user feedback. The user 8 may manually enter the information, or it may be entered automatically. In an example, the user 8 (or the user's caretaker) may enter information such as when medication was taken or what food and drink the user 8 consumed. Electronic device 19 also may include testing equipment (not shown) or an interface for receiving information from testing equipment. Testing equipment may include, for example, a blood glucose meter, heart rate monitor, weight scale, blood pressure cuff, or the like. The electronic device 19 also may include one or more sensors (not shown), such as a camera, microphone, or accelerometer, for collecting feedback from a user 8. In one example, the device may include a glucose meter for reading and automatically reporting the user's blood glucose levels.

Electronic device 19 also may include a presentation layer. The presentation layer may be a web browser, application, messaging interface (e.g., e-mail, instant message, SMS, etc.), etc. The electronic device 19 may present notifications, alerts, reading materials, references, guides, reminders, or suggestions to a user 8 via presentation layer. For example, the presentation layer may present articles that are determined to be relevant to the user 8, reminders to purchase medications, tutorials on topics (e.g., a tutorial on carbohydrates), testimonials from others with similar symptoms, and/or one or more goals (e.g., a carbohydrate counting goal). The presentation layer also may present information such as a tutorial (e.g., a user guide or instructional video) and/or enable communications between the healthcare provider, and the user 8, e.g., patient. The communications between the healthcare provider, and the user 8, e.g., patient, may be via electronic messaging (e.g., e-mail or SMS), voice, or real-time video. One or more of these items may be presented based on a treatment plan or an updated treatment plan, as described later. The presentation layer also may be used to receive feedback from a user.

The system 100 also may include one or more databases, such as a database 302. Database 302 may be implemented using any database technology known to one of ordinary skill in the art, such as relational database technology or object-oriented database technology. Database 302 may store data 302-1. Data 302-1 may include a knowledge base for making inferences, statistical models, and/or user information. Data 302-1, or portions thereof, may be alternatively or simultaneously stored in server 29 or electronic device 19.

System 100 can be used for a wide range of applications, including, for example, addressing a user's healthcare, maintaining a user's finances, and monitoring and tracking a user's nutrition and/or sleep. In some implementations of system 100, any received data may be stored in the databases in an encrypted form to increase security of the data against unauthorized access and complying with HIPAA privacy, and/or other legal, healthcare, financial, or other regulations.

For any server or server systems 29 depicted in system 100, the server or server system may include one or more databases. In an example, databases may be any type of data store or recording medium that may be used to store any type of data. For example, database 302 may store data received by or processed by server 29 including information related to a user's treatment plan, including timings and dosages associated with each prescribed medication of a treatment plan. Database 302 also may store information related to the user 8 including their literacy level related to each of a plurality of prescribed medications.

Health Conditions

Diabetes mellitus (commonly referred to as diabetes) may be a chronic, lifelong metabolic disease (or condition) in which a patient's body is unable to produce any or enough insulin, or is unable to use the insulin it does produce (insulin resistance), leading to elevated levels of glucose in the patient's blood. The three most identifiable types of diagnosed diabetes include: pre-diabetes, type 1 diabetes, and type 2 diabetes. Pre-diabetes is a condition in which blood sugar is high, but not high enough to be type 2 diabetes. Type 2 diabetes is a chronic condition that affects the way the body processes blood sugar. Lastly, type 1 diabetes is a chronic condition in which the pancreas produces little or no insulin.

Diabetes generally is diagnosed in several ways. Diagnosing diabetes may require repeated testing on multiple days to confirm the positive diagnosis of a types of diabetes. Some health parameters that doctors or other suitable healthcare providers use when confirming a diabetes diagnosis include glycated hemoglobin (A1C) levels in the blood, fasting plasma glucose (FPG) levels, oral glucose tolerance tests, and/or random plasma glucose tests. Commonly, a healthcare provider is interested in a patient's A1C level to assist in the diagnosis of diabetes. Glycated hemoglobin is a form of hemoglobin that is measured primarily to identify the three-month average plasma glucose concentration that may be used by doctors and/or other suitable healthcare providers include weight, age, nutritional intake, exercise activity, cholesterol levels, triglyceride levels, obesity, tobacco use, and family history.

Once a diagnosis of a type of diabetes is confirmed by a doctor or other suitable healthcare provider, the patient may undergo treatment to manage their diabetes. Patients having their diabetes tracked or monitored by a doctor or other healthcare provider may be treated by a combination of controlling their blood sugar through diet, exercise, oral medications, an/or insulin treatment. Regular screening for complications is also required for some patients. Depending on how long a patient has been diagnosed with diabetes, mHealth application 1 may suggest a specific treatment plan to manage their condition(s). Oral medications typically include pills taken by mouth to decrease the production of glucose by the liver and make muscle more sensitive to insulin. In other instances, where the diabetes is more severe, additional medication may be required for treating the patient's diabetes, including injections. An injection of basal insulin, also known as background insulin, may be used by healthcare providers to keep blood glucose levels at consistent levels during periods of fasting. When fasting, the patient's body steadily releases glucose into the blood to supply the cells with energy. An injection of basal insulin is therefore needed to keep blood glucose levels under control, and to allow the cells to take in glucose for energy. Basal insulin is usually taken once or twice a day depending on the type of insulin. Basal insulin acts over a relatively long period of time and therefore is considered long acting insulin or intermediate insulin. In contrast, a bolus insulin may be used to act quickly. For example, a bolus of insulin that may be specifically taken at meal times to keep blood glucose levels under control following a meal. In some instances, when a doctor or healthcare provider generates a treatment plan to manage a patient's diabetes, the doctor creates a basal-bolus dose regimen involving, e.g., taking a number of injections throughout the day. A basal-bolus regimen, which may include an injection at each meal, attempts to roughly emulate how a non-diabetic person's body delivers insulin. A basal-bolus regimen may be applicable to people with type 1 and type 2 diabetes. In addition to the basal-bolus regimen requiring injections of insulin, the treatment plan may be augmented with the use of prescribed oral medications. A patient's adherence to a treatment plan may be important in managing the disease state of the patient. In instances where the patient has been diagnosed with diabetes for more than six months, for example, a very specific treatment regimen must be followed by the patient to achieve healthy, or favorable, levels of blood glucose. Ultimately, weekly patterns of these medication types of treatments may be important in managing diabetes. mHealth application 1 may recommend treatment plans to help patients manage their diabetes.

Exemplary Methods

Figure 4:
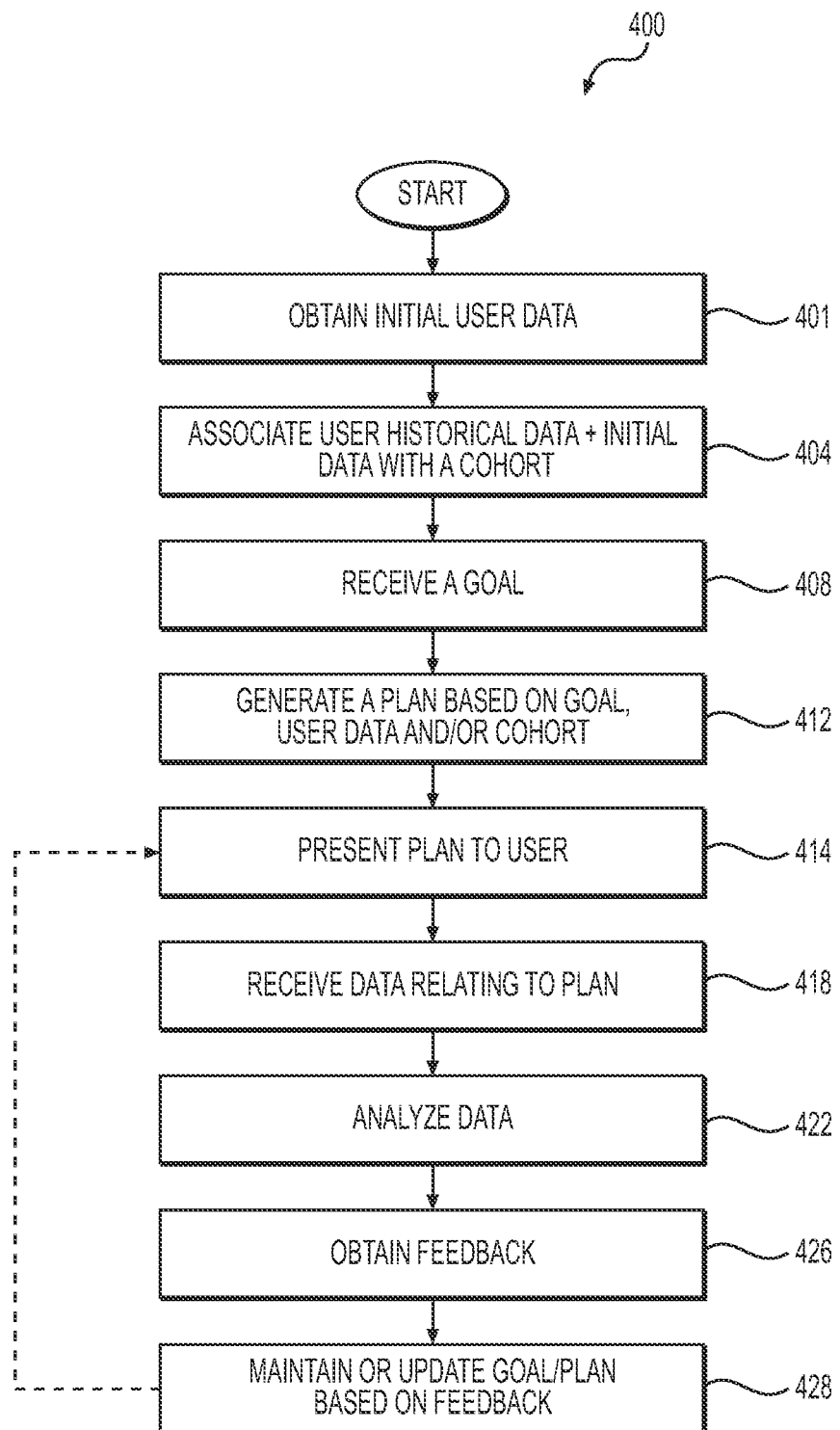
FIG. 4 is a flowchart of a health management method, according to an example of the present disclosure.

FIG. 4 is a flow diagram of an exemplary method 400 for providing a treatment recommendation. In some examples, the depicted method 400 may be used for automatic clinical-decision making. As shown in FIG. 4, at step 401, electronic device 19 and/or server 29 may obtain initial data from a user 8 before generating a treatment plan. The user 8 may enter the data into the electronic device 19, which may be sent to server 29. In some examples, at step 401 in FIG. 2, server 29 may receive data that is relevant to a healthcare provider, e.g., a doctor may enter related patient healthcare information into server 29. This data may be electronically transmitted by the provider and/or the user 8 and received by the server 29 at step 401. The data may be electronically transmitted and received by the server 29 at step 401 in any suitable manner. For example, the provider may access mHealth application 1 or secure server and send or drop electronic data files via a network so that the files may be accessed by mHealth application 1. In some examples, the provider may allow mHealth application 1 limited access, in compliance with any healthcare privacy regulations and other applicable regulations, to any electronic medical records, user prescription records, referral records, etc. In some examples, the service may electronically retrieve healthcare data from such electronic records (e.g., automatically). In other examples, user data may be electronically transmitted by a user 8 and may be electronically received by the service in any suitable manner. The user data may be manually input by the user 8 via mHealth application 1 and/or may be automatically retrieved by the service from an electronic device of the user (e.g., device 19) that may measure user health values, such as heart rate, blood glucose, blood oxygen, blood pressure, activity, stress, mood, and/or sleep either periodically or continuously. In some examples, the user 8 may be required to complete a questionnaire and/or survey at step 401. The questionnaire may be presented to the user 8 during the setup of mHealth application 1.

In another example, initial data may be received from other application software downloaded to a device 19 (e.g., an application on a smart phone corresponding to a fitness band tracker used to collect data on calories burned, steps walked, or the like, by the user 8). This initial data may be collected from the other application software either periodically or continuously throughout method 400.

The data received by the server at step 401 may be stored in a database (e.g., database 302 of FIG. 3). The data may be accessed at any time and may be displayed, printed, or updated in any suitable manner. The stored data may be organized and accessed in any suitable manner. In some examples, the data may be electronically tagged with various identifiers, such as age, gender, clinical condition, etc.

The initial data may include an identification of one or more disease states of the user 8 and/or other parameters associated with the health of the user 8. For example, initial data may include a diagnosis of diabetes selected from the following types: type 1, type 2, pre-diabetes, gestational diabetes, early on-set diabetes, late adult on-set diabetes, etc. Initial data may include blood glucose level, hemoglobin A1C level, blood pressure value, low-density lipid level, high-density lipid level, triglyceride cholesterol level, total cholesterol level, body mass index (BMI), age, weight, tobacco use, alcohol use, exercise activity (e.g., step count, calories burned, heart rate), and stage of diabetes/severity of disease. Other types of data also may be included. In some examples, the initial data may include a length of time that the user 8 has been diagnosed with a disease, such as, e.g., diabetes. The initial data received at step 401 also may include other relevant data of the user 8, including a clinical profile of the user 8 such as history of diseases, significant medical events (e.g., heart attack, stroke, head trauma, transplant), lab values, user self-reported clinical, behavioral and psycho-social data, user's demographics, medical history. In one example, when the disease is diabetes, relevant data of the user may be clinical data of the user since the original diagnosis, and also may include clinical data of the user from before the original diagnosis. In this example, if the user 8 has had type-2 diabetes for the 20 years, the relevant historical data may include at least the user's A1C levels and/or blood glucose levels during those 20 years. Other suitable data sets that may be collected include metabolic data (e.g., blood pressure, blood glucose, weight, LDL, lab results, and the like), medication (e.g., dose, frequency, class of medication), symptoms (e.g., structured and unstructured inputs), diet (e.g., food, calories, protein, fat, carbohydrates, sodium, allergies, and the like), activity (e.g., type, duration, intensity, and the like), and psychosocial (e.g., financial, claims, beliefs, barriers, and the like).

For any data collected from the user 8 at step 401, metadata may be extracted from the stored data. In some other examples, the system, the device, and/or the server may suggest places to eat based on geo-tagging results of the user 8 (e.g., provide the user 8 with recommendations for restaurants in proximity to the user 8 with healthy menu options). In some examples, based on geo-tagged restaurants, restaurant menu data can be extracted, and healthier menu options from the menu data can be presented to the user 8 (e.g., menu items containing low sugar or no sugar can be presented to the user). In some examples, restaurant meal data may be entered into server 29 and/or device 19 by the user 8. In both examples, meal options may be presented to the user 8 based on the restaurant meal data based on, for example, time of day, information on the user's eating habits, user personal preferences, medications, and/or exercise.

Initial data also may include medications the user 8 is currently taking (e.g., oral medications, basal injections and/or bolus injections) and data related to the user's health and lifestyle, such as, e.g., adherence history to prescribed medication (e.g., glycemic, oral insulin, etc.), adherence history to prescribed medication dosage (e.g., glycemic, oral insulin, etc.) correlated to its effect on said blood glucose level, carbohydrate intake, weight, psycho-social determinants, and blood glucose level testing frequency correlated to its effect on said blood glucose level. In some examples, a user's history of engagement frequency with the electronic device 19 also may be used in the initial user data. For example, mHealth application 1 may generate a more complex treatment plan if the user 8 shows a high engagement frequency with electronic device 19. The initial data also may include data input by a healthcare provider, and may include subjective opinions of the user 8 by the healthcare provider. For example, the data may include the healthcare provider's subjective opinions regarding the user's motivation, compliance, overall health, and the like. mHealth application 1 may weigh the subjective opinions of the provider when creating a treatment plan. For example, if the provider's subjective opinion of the user 8 is that the user 8 has a high compliance to medication and dietary regimens, but a low compliance to exercise regimens, then a subsequent treatment plan generated by mHealth application 1 may include a larger emphasis on medication and diet, as opposed to exercise. Additionally, mHealth application 1 also may use this information to focus tutorials and educational content sent to the user 8 on exercise topics and the benefits of exercise relative to the user's health.

At a step 404, and based on the data from step 401, the server 29 may associate the user 8 with a cohort of other users (e.g., a group of users having similar physical, medical, psycho-determinant conditions) based on similarities between the user 8 and other users. For example, a male having a height of 70 inches, weighing 190 pounds, and having high blood pressure, Indian ethnicity, type-2 diabetes, and an A1C level of approximately 6.8%, may be associated with users of a cohort having similar characteristics. As previously disclosed, a user 8 with an A1C level of greater than 6.5% is considered diabetic. A cohort, in this example, could be a group of Indian American males having similar blood pressures, heights, weights, and A1C levels that have responded well to a particular treatment plan and/or responded poorly to other plans. For example, a group of males of Indian ethnicity, 68-72 inches tall, weighing 175-200 pounds, may respond well to an oral medication treatment for type-1 diabetes if the medication is taken twice daily at a particular dosage and time schedule. As set forth below, goals and/or treatment plans may be assigned to the user 8 based on the association with the cohort based on results or goals/treatments of the users within the cohort. A doctor or other suitable healthcare provider, or mHealth application 1 itself, may establish a goal and/or treatment plan based on goals and/or treatment plans that were successful within the cohort to treat a specific medical condition. In some examples, a cohort may include a small number of users, e.g., two users, while in other examples, a cohort may include more users, e.g., dozens, hundreds, or thousands. Depending on the specific medical condition or chronic disease, the doctor or other suitable healthcare provider wishes to address, the cohort may change.

Then, in a step 408, mHealth application 1 may receive one or more goals from the user 8 or other suitable healthcare provider, or mHealth application 1 may generate a goal based on the initial data received. In other examples, the goal may be a default goal, such as, e.g., lowering blood glucose levels of the user 8 when the application is a blood glucose management application. The goal may include improving one or more health parameters of the user, such as, e.g., blood glucose level, hemoglobin A1C level, blood pressure, low-density lipid level, high-density lipid level, triglyceride cholesterol level, total cholesterol level, body mass index (BMI), weight, user activity level, sleep duration, sleep quality, adherence to prescribed medication, nutrition (e.g., carbohydrate intake), psycho-social determinants, and blood glucose level testing frequency correlated to its effect on said blood glucose level, among others. The goal may be determined by mHealth application 1 based on the previously entered information, including information based on the user's disease state, history of user's disease, and/or other initial user data received at step 401. The goal also may be determined based on the cohort associated with the user 8 at step 404. One or more machine learning algorithms may be used by the server 29 to help determine the goal. In some examples, goal may include a time period after which the goal should be achieved. For example, the goal may be to lower a user's A1C level by a certain amount over a fixed time period (e.g., a treatment window to alleviate a specific health parameter of the user 8). In some examples, the fixed time period may be one day, one week, one year, or any other suitable time period. In some examples, the time period may be expanded or reduced by mHealth application 1 based on the user's progress or compliance over the course of the time period. For example, mHealth application 1 may reduce a fixed treatment window from 20 weeks to 16 weeks if the user's A1C levels are responding to a specific treatment earlier than anticipated.

The goal, at step 408, also may include multiple parameters that should be improved over the course of the treatment window. For example, a user 8 may set a goal of losing 10 pounds and to drop her A1C level from 6.7% to 6.3% over a 12 week time period. In another example, mHealth application 1 may set a goal to reduce the user's total cholesterol level over a 20 week time period, in addition to reducing their blood pressure to a normal level, e.g., 120/80 mm Hg from an elevated level. In this example, mHealth application 1 may expand the 20 week window if the user is not on track to meet their goal over the original 20 week window. For example, at week 15, mHealth application 1 may increase the time period for the user 8 to reach their goal to 30 weeks if the health parameter is determined to be unattainable within the original time period.

In some examples, the goal or goals may change over the time period. For example, over a time period of 12 weeks, the goal may change weekly based on the results achieved by the user 8 in previous weeks, the effectiveness of a treatment plan, and based on a compliance of the user 8 to various portions of the treatment plan. Upon the completion of each of the 12 weeks, the goal may be summarized into a summary or report and presented to the user 8 and/or the user's doctor or other suitable healthcare provider. In some examples, mHealth application 1 may prompt the user 8 to change the goal. In some examples, the goal may be changed automatically by mHealth application 1. In some examples, mHealth application 1 may provide suggestions to the user. For example, based on the data received from a cohort, mHealth application 1 may suggest to the user 8 to reduce their blood pressure within the time period originally prescribed by their doctor or other suitable healthcare provider. The goal also may be based on the user's personality traits as determined by results of the questionnaire that the user 8 has completed at step 401. For example, if the results of the test indicate that the user 8 is highly motivated, the goal may be set higher than if the results of the questionnaire indicated that the user 8 is not highly motivated (e.g., the time period for addressing or alleviating the user's weight reduction from 195 pounds to 185 pounds can be reduced from 16 weeks to 12 weeks.

Next, at a step 412, based on the initial user data, cohort and/or the goal, from steps 401, 404, and 408, respectively, mHealth application 1 may generate a treatment plan for the user 8. It is appreciated that the treatment plan may be based on a perceived best combination of mechanisms based on user preferences, empirical data, data collected from other users (e.g., a cohort of step 404), or the like. The treatment plan may include a schedule of activities to be performed by the user 8. mHealth application 1 may be configured to send reminders and notifications to the user 8 to help ensure user compliance with the treatment plan. For example, the plan may include instructions to record blood glucose values before and after a morning meal. In such cases, mHealth application 1 may be configured to send a notification to the user 8 (via the application, text message, email, or telephone call) to remind the user 8 to eat the morning meal and to record blood glucose values.

In some examples, when the user 8 fails to comply with one or more portions of the treatment plan, mHealth application 1 may be configured to lock access to other features of the user's device until user 8 complies with the treatment plan. When the user device is a phone, mHealth application 1 may be configured to lock access to certain functionality of the phone until the user 8 satisfies certain steps of the treatment plan (e.g., entering a blood glucose value).

The treatment plan at step 412 may be generated based on goals (at step 408) mHealth application 1 receives from or sets for the user 8. For example, when the goal is related to lowering A1C and/or blood glucose levels, the plan may include blood glucose testing, meal logging, exercise activity, sleep activity, medication(s) logging, educational curriculum activity (e.g., tutorials completed on disease management), assessments/questionnaires, and other software application features. In an example where the user 8 has diabetes, the goal or goals may guide the user 8 to execute one or more of the following tasks: test blood glucose, e.g., in pairs (before and after meals, exercise, or fasting), log meals (e.g., carbohydrate intake) and corresponding meal times, log exercise activity (e.g., log steps taken in a day or week or other suitable time period), log sleep activity, and log type, timing, and dosage of medication consumed from a predetermined medication regimen (e.g., oral insulin once a day and a bolus insulin injection once a day).

The treatment plan also may include prescribing or recommending types and dosages of medication, in addition to scheduling when the medication should be consumed by the user 8. The treatment plan also may set dietary guidelines for the user 8 to help manage both weight and blood glucose levels of the user 8. The dietary guidelines may include calorie guidelines (e.g., calorie, carbohydrate, and sodium limits, and water guidelines), food type guidelines (e.g., no more than 15 percent of calories from processed sugar), and timing guidelines (e.g., when food or drink should be consumed). In an example, the treatment plan may include presenting a weekly summary to the user 8 via mHealth application 1. The weekly summary may display blood glucose levels over the course of the week, carbohydrate intake amounts and times consumed, medication regimen and adherence, exercise activity, sleep activity, steps activity, and other wellness activities (e.g., time spent performing yoga or meditation). A weekly summary may include a display of a cause and effect analysis of dependent variables (e.g., carbohydrate intake, exercise activity, sleep activity, medication intake, adherence to medication, etc.) on independent variables related to diabetes disease management. In one example, insights from the weekly summary may be provided for generic educational purposes targeted towards a user's lifestyle and change in behavior (e.g., psycho-social determinants, including distress, disability, financial/economic conditions, etc.).

The user also may be presented with a daily educational lesson via mHealth application 1. In some examples, the lesson may be related to a diabetes management curriculum, which covers knowledge, skill and behavior around AADE 7 self-help behaviors created by the American Association of Diabetes Educators. In some examples, the user 8 also may be presented with daily food recipes tailored to management of a blood glucose disorder (e.g., low carbohydrate recipes).

The treatment plan may be administered over a time period. The time period may be determined by mHealth application 1 or determined by the user 8 or healthcare provider. The treatment period may be a fixed time period or may be variable. In a variable time period, mHealth application 1 may extend or shorten the time period for which the treatment plan is administered.

Meal information, including fasting and/or carbohydrate intake, or medication information may be required by mHealth application 1 as part of the treatment plan. Meal information may include number of calories consumed, grams of carbohydrates consumed or other related nutritional data useful in the management and/or treatment of diabetes. The treatment plan also may include a schedule for when food should be consumed. In addition, variables such as food allergies or religious preferences can be used to refine dietary recommendations. For example, if a patient will be fasting in observance of her religion, mHealth application 1 can account for that during the day, and suggest smart dietary choices for the evening.

Medication information may include types of diabetes drugs prescribed to the user 8, dosages, over-the-counter medication intake by the user 8, times that the drugs should be consumed, and other related data about the medicine(s) consumed helpful in the management and/or treatment of diabetes. In a treatment plan, meal or medication information may be requested at specific times during a user's day, week or other suitable treatment plan time period. Furthermore, the user 8 may be required to provide the aforementioned data during both weekday(s) and weekend(s) for comparison.

Blood glucose (or blood sugar) may be an important measure of the user's health. In the U.S., blood sugar is normally measured in milligrams of glucose per deciliter of blood (mg/dl). For someone without diabetes, a fasting blood sugar on awakening should be under 100 mg/dl. Before-meal normal sugars are 70-99 mg/dl. "Postprandial" sugars taken two hours after meals should be less than 140 mg/d. For blood glucose monitoring, the user's blood glucose may be measured at an isolated time, or in pairs, in order to track any spike or abnormality between. For example, when the user's blood glucose is measured in pairs, the blood glucose is determined before the user 8 has a meal and immediately thereafter. In one example, at least 20% to 33% of the data requested by the treatment plan must be collected from a weekend. For example, in the following scenarios 1) when three blood glucose meal pairs are required, one meal pair must be from a weekend, 2) when three fasting blood glucose pairs are required, one fasting blood glucose measurement must be from a weekend, 3) when four blood glucose pairs are required, one meal pair must be from a weekend, 4) when five blood glucose meal pairs are required, one meal pair must be from a weekend, and 5) when two fasting and two meals are required, any one (fasting or meal) must be from a weekend.

For meal activity, a treatment plan may be generated to provide a meal intake regimen. For example, in the first two weeks of the treatment plan time period, a user 8 may be asked to fast three times a week, have seven total meals with at least three meals being different (e.g., breakfast, lunch, dinner, snack, bedtime snack), and reduce or eliminate the intake of specific food groups (e.g., carbohydrates) determined by mHealth application 1. In an example, a treatment plan can present a user 8 daily and/or weekly recipes. Recipes, for example, may include ingredients or items found to address a user's disease state (e.g., low-sugar or no-sugar recipes).

For exercise activity, a treatment plan may be generated to provide a specific exercise regimen determined by mHealth application 1. For example, treatment plan may require the user 8 to exercise twice in one week. In another example, the exercise activity may require the user 8 to take a minimum number of steps daily or weekly. The treatment plan can be modified by mHealth application 1 if the user 8 decides they do not wish to exercise at all during their treatment plan or if mHealth application 1 determines that the user's compliance to prescribed exercise is low. In this example, mHealth application 1 may suggest an alternative treatment plan. For example, the treatment plan may increase a medication dosage and increase paired fasting meals to lower blood glucose in lieu of the exercise that was originally prescribed.

For educational curriculum activity, a user 8 may receive one or more tutorials, videos, or lessons on an electronic device 10. In an example, one lesson may cover a knowledge, a skill, and/or a behavior related to a topic. The educational content may be divided into subject areas (e.g., healthy eating, being active, taking medication, monitoring, problem solving, reducing risk, healthy coping, etc.). Each subject area may include knowledge, skill, and behavior components. For the subject area, "healthy living," for example, the knowledge component may include: education on a healthy meal plan, and benefits of balanced meals; the skill component may include: carbohydrate counting, and develop an eating plan; and the behavior component may include: meal logging, preventing high/low blood glucose (BG), and insights into healthy eating. For the subject area, "being active," for example, the knowledge component may include: benefits of being active; the skill component may include: presenting simple ways to be more active, and goal setting; and the behavior component may include: tracking activity, monitoring weight, and insight of the effect of activity on BG. For the subject area, "taking medication," for example, the knowledge component may include: educating on different types of meds, and medication tips; the skill component may include: medication lists, and setting reminders to take medication; and the behavior component may include: scheduling and recording medications, and insight into medication adherence. For the subject area, "monitoring," for example, the knowledge component may include: educating on monitoring BG; the skill component may include: when to check BG, and what do the numbers mean; and the behavior component may include: logging BG, pair checking, and insight into BG. For the subject area, "problem solving," for example, the knowledge component may include educating on diabetes solving cycle; the skill component may include: success stories, and education on diabetes resources; and the behavior component may include: insight into the user's diabetes management, and recommendations. And, for the subject area, "reducing risk," for example, the knowledge component may include: educating on reducing risk; the skill component may include: ways to record health information, and tracking preventative care; and the behavior component may include: insight into the user's health information, and reminders to track information.

For sleep activity, a treatment plan may be generated to provide a sleep cycle regimen. For example, in the first two weeks of the treatment plan time period, a treatment plan can prompt the user 8 via electronic device 19 to acquire a minimum number of hours of sleep per night (for example, mHealth application 1 may determine someone with type-2 diabetes that engages in an above-average level of exercise should be getting at least 8-9 hours of sleep per night during the duration of the treatment plan). In an example, a doctor or other suitable healthcare provider can also edit or contribute to a user's sleep cycle regimen.

At step 412, medication intake also may be part of the treatment plan. For example, a treatment plan may be generated to provide a medication regimen to the user 8. The treatment plan may prescribe the user 8 to take an oral insulin tablet once before his first meal and once directly after his last meal of the day. Additionally, in the example, the treatment plan may recommend the user 8 take a bolus insulin injection after any meal considered by the treatment plan to contain a high level of carbohydrates. In some examples, the regimen may be augmented with meal logging activity and meal pairs. For example, in the first two weeks of the treatment plan time period, a user 8 may have daily meal pairings, requirements for fasting at certain meal times, an oral tablet regimen, and bolus/basal insulin injections if mHealth application 1 determines that additional insulin is necessary. Adherence to the medication regimen also is an objective of the treatment plan.

For any of the above-identified activities that are part of the treatment plan, including blood glucose, exercise activity, sleep cycle activity, medication intake and adherence activity, data can be provided to, or requested by mHealth application 1, in pairs or as single events. For example, when blood glucose monitoring is part of a user's treatment plan, mHealth application 1 may prompt a user 8 to provide his blood glucose measurement after his first meal of the day, and on numerous other occasions. In other examples, mHealth application 1 may prompt the user 8 to provide his blood glucose measurement in a pair, e.g., the blood glucose be measured directly before a meal and directly after the meal. It can also be appreciated the treatment plan may utilize one or more prompts via mHealth application 1 to remind the user 8 of requirements of the treatment plan. For example, for a user 8 requiring short acting insulin only, a treatment plan may ask a user 8 to test for initial blood glucose, send a pair follow-up reminder two hours later, or else request to schedule the pair follow-up immediately before a meal (e.g., pre-meal). In this example, if the pair is done correctly, the treatment plan requests the user 8 to schedule to have a different meal the next day. In a second example, for a user 8 requiring long acting insulin, the treatment plan may ask a user 8 to test his blood glucose early in the morning, and based on the result of the reading, suggest a fasting and/or oral insulin tablet and/or a bolus insulin injection. In other examples, mHealth application 1 can plan a dynamic reminder schedule to prompt a user 8 to accept the fasting schedule and meal pairing schedule for the day based on the user's testing journey. In another example, reminders can be used if the user 8 misses a scheduled test. In other words, if the user 8 misses his reminder to test his blood glucose, he may be prompted to re-attempt testing at his next meal (or meal pair) or day (fasting). Other task prompts include videos, articles, touch point messages, recipes, and any other suitable prompt based on the user's input or interests. In an example, one task prompt may be provided to the user 8 daily.

Next, at a step 414, the treatment plan to the user 8 on the electronic device 19 via mHealth application 1. For example, the treatment plan may be presented on a graphical user interface (GUI) on the electronic device 19. In some cases, the plan may be summarized and presented as a weekly plan. The plan may present daily or weekly challenges or goals to help focus and motivate the user 8. For example, the plan may suggest to the user 8 to improve blood glucose level over the next seven days by exercising five times, fasting three times, and adhering to a medication regimen of two oral tablets per day, including one basal injection per day.

Next, at a step 418, mHealth application 1 may receive data relating to the plan. The data may be manually input by the user 8 via electronic device 19. For example, the user 8 may be required to designate the time that a blood glucose level was taken, in addition to the value of the blood glucose level itself. The user 8 also may be required to manually enter a number of steps walked during that day. In other examples, the data may be retrieved from paired electronic devices (e.g., an exercise tracker) and/or retrieved from other applications. Data may be continuously transmitted to the server 29 in real-time by the electronic device 19 whenever the two are in data communication. In an example, weekly reports of a user's meal logging activity, sleep activity, and blood sugar levels are reported to the server 29. In this example, data will be stored on a memory of electronic device 19 and will be transmitted to server 29 once data communication is restored.

The data collected at step 418 may include updates of any of the data received at step 401, or any of the data required by the treatment plan generated at step 412. Data also may be obtained that is non-specific to the user 8, such as weather conditions, current events, date, and/or season. This non-specific data may be used to improve the accuracy of the recommendation. For example, if the real-time data indicates that the temperatures for the last ten days where the user 8 lives have been below −10 degrees Fahrenheit, mHealth application 1 may not recommend that a user 8 start exercising outside as it may be too cold to exercise outside.

Next, at a step 422, data from the plan, which is stored on the server 29, may be analyzed, e.g., by one or more machine learning algorithms. At step 422, mHealth application 1 may determine compliance of the user 8 with each prescribed activity (e.g., one or more of the activities described previously, including diet, BG monitoring, medication, exercise, etc.). Adjusting the user's goal(s) and/or treatment plan based on compliance with each prescribed activity, or other suitable aspect, of the original goal and/or plan. In an example, adherence to a user's medicine regimen can be analyzed to determine if the user 8 is not compliant with the prescribed regimen of the user's original treatment plan. mHealth application 1 may determine a user's compliance to each aspect of the treatment plan, such as, e.g., compliance to the diet, medication, exercise, and sleep portions of the treatment plan.

In step 422, for example, various algorithms may be applied to the data to learn from by analyzing the data. In some examples, machine learning algorithms and/or other higher-level algorithms (e.g., supervised and unsupervised learning algorithms) may be applied to the data to learn and otherwise extract information from the data, such as for use in learning provider decision-making patterns and behaviors and/or user 8 behavioral patterns. Examples of such machine learning algorithms may include artificial neural networks, Bayesian statistics, case-based reason, decision trees, inductive logic processing, Gaussian process regression, Gene expression programming, Logistic model trees, stochastic modeling, statistical modeling (e.g., Bayesian networks, Markov models, ANOVA, etc.), and/or any other suitable algorithm or combinations of algorithms. For example, at step 422, machine-learning algorithms may be applied to the data to learn the characteristics of users for which the provider has prescribed or modified use of a drug, provided a referral to another provider, recommended a lifestyle change (e.g., exercise, diet, educational tutorials on disease management and/or stress management).

The machine learning algorithms applied at step 422 may detect any patterns, idiosyncrasies, or any other significant associations that may be used in generating a decision model that mimics or attempts to understand the decision-making of the provider and/or predicted behavior of the user 8. In another example, the machine-learning algorithm may identify a user cohort for whom components of a treatment plan may be effective, ineffective, or partially effective.

The analysis may identify patterns between any of the different data sets received by the user 8. For example, the analysis may identify triggers that are indicative of a negative consequence on the user's health. For example, the analysis may identify that the user 8 has low compliance to one or more aspects of the treatment plan on a certain day or days of the week, e.g., that the user 8 has low compliance on Fridays, or more specifically, on the third Friday of every month. This identification of a trigger (Friday) may correspond to events in the user's life that are not able to be otherwise captured by mHealth application 1. For example, the third Friday of every month may be a particularly event-filled day for the user 8, resulting in low compliance with the treatment plan and/or poor dietary habits, etc. The identification of this trigger may allow mHealth application 1 to send notifications and/or reminders on subsequent Fridays, or third Fridays of a month, to help improve user compliance with the plan. For example, the identified pattern may be presented to the user 8 with a warning or suggestion to the user 8 to consider why compliance is low in response to the trigger.

Other triggers include, for example, the time or intensity of certain exercise. That is, mHealth application 1 may identify that the user tends to experience negative effects on overall blood glucose levels and health when the user takes too many steps. While this may be counterintuitive, a particular user may show a correlation between over-exercising and over-eating, or over-exercising and failing to comply with other portions of the treatment plan.

In other examples, mHealth application 1 may determine causal relationships between pairs of independent and dependent variables, such as, e.g., blood glucose values and engagement frequency, medication adherence and engagement frequency, variance in blood glucose and exercise duration, and the like. For example, mHealth application 1 may send the user a notification on Thursday evenings to remind the user that their compliance is generally low on Fridays.

In other examples, reverse kinematics may be utilized by using known values for key signals, and patterns from those signals to help chart choices in therapeutic pathways for patients. For example, by knowing current blood glucose values and blood glucose transfer functions, mHealth application 1 may suggest alternatives to reduce blood glucose values of the patient including, but not limited to medication, exercise, and other mechanisms. Thus, mHealth application 1 may provide options for therapy using values and pre-defined constraints.

In some examples, blood glucose and A1C values may be mapped to dependent variables. For example, blood glucose and A1C values may be mapped to activity (e.g., duration and intensity and their effect on blood glucose), sleep (e.g., duration and quality), adherence to prescribed glycemic medication and dosage, carbohydrate intake (e.g., high carbohydrate intake correlated to increase in blood glucose), weight (e.g., weight loss and increase correlated to increase and decrease in blood glucose, respectively), psycho-social determinants (e.g., emotional stress, social determinants, material needs), testing frequency (e.g., increase or decrease correlated to an effect on blood glucose control), and engagement frequency (e.g., increase or decrease in user engaging with mHealth application 1 and its effect on blood glucose control).

In one example, mHealth application 1 may display to the user 8 the impact and correlation of carbohydrates, activity, sleep, and medication adherence to weekly blood glucose values in a single view or a single screen. The user 8 may select a specific dependent variable (e.g., carbohydrates), to show a calendar view week graphic with a guided explanation for an action to be taken by the user 8 (e.g., a treatment recommendation for reducing carbohydrate intake in the future). If the user 8 instead selected "activity," as the variable for further analysis, mHealth application 1 may provide a detailed view and recommendation showing how an increase in activity lowers blood glucose levels for the user 8.

In another example, blood pressure may be mapped to its dependent variables. For example, blood pressure may be mapped to activity (e.g., duration and intensity and their effect on blood pressure), sleep (e.g., duration and quality and their impact on blood pressure), blood pressure medications (e.g., adherence to prescribed blood pressure medication and its effect on blood pressure), sodium (e.g., sodium intake correlated to increase or decrease in blood pressure), weight (e.g., weight loss and gain correlated to an increase or decrease in blood pressure), and psycho-social determinants (e.g., emotional stress, social determinants, and material needs correlated to blood pressure control).

In another example, lab or lipid values may be mapped to their dependent variables. For example, lab or lipid values (e.g., LDL, HDL, triglycerides) may be mapped to activity, lipid medications, food, fat, calories, and weight, in a substantially similar manner as set forth above with respect to blood glucose and blood pressure mapping.

Other primary independent variables that can be mapped to various dependent variables include testing frequency (e.g., the number of times a patient will test their blood glucose over a period of time (per day, per week)), exercise duration, intensity and frequency (e.g., the capturing, whether manual or through a sensor (e.g., FitBit, Jawbone, SHealth, iHealth, etc.)) of exercise information that is pertinent to a patient's diabetes or other health, intervention modality, frequency, and duration (e.g., the mode by which a patient engages with managing their diabetes (e.g., testing their blood glucose values, watching a video about their medication, listing to an audio clip from a doctor (SME) getting a real-time or longitudinal message on mHealth application 1, etc.)) and the frequency and durations of such engagement transactions, engagement frequency (e.g., the number of time a patient uses the product or interacts with the product over a predefined period of time (e.g., per week, per day, etc. —a mere login may or may not constitute engagement), sleep duration and quality (e.g., the capturing of sleep data from an automated sensor that captures length of sleep and quality (e.g., light, medium, heavy, REM, or the like)), food quality and quantity (e.g., the capture of what food was consumed by name, category, portion serving, and the carbohydrates, protein, fat, calories, and sodium content therein), medication adherence (the capture of the patient's medications by drug name, dose consumed, dose prescribed, time of consumption, time prescribed (e.g., take it with breakfast, lunch, etc.)), time of day/reading type/season (e.g., the temporal attributes of the engagement—what time of week, time of day, season, etc., and reference to the activity (e.g., before a meal, after a meal, before exercise, before bed, etc.)), location (e.g., the GPS locator (latitude and longitude) of where the transaction and engagement occurred or is occurring), notes (e.g., the capture of both structured as well as unstructured information that further provide context to the quantitative data being captured (e.g., a blood glucose of 400 may have context of "I ate at a restaurant," "I ate too much," but can also have free-style notes that are entered by the patient)), demographics (e.g., the series of typical descriptions for the patient—age, race, gender, income), genomes (e.g., the genomic profile of the patient), and technology modality (e.g., the technology that is being used to capture the engagement (e.g., smart phone, tablet, PC, smart TV, etc.)).

Primary dependent variables include A1C (e.g., hemoglobin A1C), blood glucose (e.g., instantaneous blood glucose), blood pressure (e.g., instantaneous blood pressure), lipid (e.g., lab-measured values of LDL, HDL, and triglyceride cholesterol), BMI, and weight. Any of these variables can be represented as an ordinary value, a delta (change) value, or rate of change (first derivative).

Upon identification of the one or more triggers that negatively affect the blood glucose levels or health of the user 8, the one or more triggers (and subsequent results of those triggers occurring) may be displayed to the user 8 via mHealth application 1. That is, after a pattern is identified, when mHealth application 1 detects events that tend to lead to negative outcomes on the user's health, mHealth application 1 may notify the user 8. For example, mHealth application 1 may send the user 8 a notification on Thursday evenings to remind the user 8 that their compliance is generally low on Fridays.

In another example, mHealth application 1 may identify that in the past week, the user 8 displayed a pattern of low fasting blood sugar. In this example, the user 8 may be prescribed an insulin with both a fast-acting component and a long-acting component. mHealth application 1 may determine that the user's hypoglycemia is most likely due to the long-acting component of the previous day's dose, and that because the low morning readings have persisted, that the user 8 should contact his provider for an insulin adjustment.

In another example, a user 8 that is prescribed insulin having both a fast-acting component and a long-acting component may experience hypoglycemia during the day but not before eating. In this situation, mHealth application 1 may determine that the fact-acting component of the user's insulin regimen may need adjustment, and may inform the user 8 and/or provider of this recommendation.

In another example, mHealth application 1 may identify that the user 8 has high blood glucose levels after meals, and may recommend that the user's dose of fast-acting insulin be adjusted. mHealth application 1 also may recommend dosage changes to long-acting insulin (e.g., Lantus) and to Metformin based on the user's blood glucose levels early in the morning and before meals.

In another example, mHealth application 1 may identify that the user 8 has low blood sugar after exercise, and may recommend that the user 8 consume a small amount (e.g., 15 g) of fast-acting carbohydrates before exercise.

In yet another example, mHealth application 1 may identify a trend between sleep and fasting blood glucose levels. In particular, mHealth application 1 may determine that fasting blood glucose values of the user 8 are negatively affected by a lack of sleep.

Next, at a step 426, the service may receive electronic feedback on the treatment plan. The feedback may be in the form of an evaluation by the provider and/or the user 8 on the treatment plan. In some examples, an evaluation form soliciting feedback on the treatment plan may be sent by the service for completion by the provider and/or user 8 at the end of each week. The evaluation may include an indication of whether or not the treatment plan was followed, a rating of the treatment plan, an explanation of the why the treatment plan was followed or why it was not followed. The evaluation form may be in the form of a multiple choice questionnaire, game, video, or other output.

Referring to FIG. 4, the method may proceed to step 428, where mHealth application 1 may use the results of the analysis and feedback to develop one or more updated plans for a user 8. The goal, at step 408, also may be updated based on the feedback (e.g., a goal was not achieved within a time period of the treatment plan). The plan and/or goal may be maintained or updated based on compliance by the user 8 with the originally prescribed plan and/or goal, the effectiveness of the plan and feedback obtained in step 426. In an example, the plan and/or goal(s) may be maintained or updated based on the time remaining in a treatment plan time period. For example, if the blood glucose levels of the user 8 have not improved after week six in a treatment plan time period of 12 weeks, the user 8 may receive an updated goal/treatment plan. The new treatment plan may be less ambitious or otherwise may be more attainable in achieving the desired goal (e.g., a specific blood glucose level). In another example, the originally prescribed medication regimen and/or any other portion of the treatment plan can be altered or modified by mHealth application 1.

In some examples, if the user's compliance is low in certain areas, the treatment plan may be updated to reduce emphasis on the user's low compliance areas. For example, low compliance in exercise activity for extended periods of time may be an indication of the user's lack of interest in exercising as part of her health management plan. Low compliance could also reflect an inability to perform portions of the exercise regimen, e.g., due to immobility, injury, weather, or the like. After such a determination is made, more emphasis may be placed on restricting a diet and increasing medication dosage, particularly where the user 8 has shown an aptitude for high compliance with dietary and medication regimens.

mHealth application 1 may discover trends by using known data to draw insights, using pattern recognition and pattern analysis, and correlation and causation. mHealth application 1 may adapt by using learning techniques to provide new insights and choices for optimizing outcomes to provide dynamic and guided pathway planning. mHealth application 1 may inform users by data capture, data logging, data analysis, and data reporting. mHealth application 1 may extrapolate by using existing data to model patterns and predict future occurrences of events, and by performing predictive modeling.

In one example, mHealth application 1 may display a weekly blood glucose/carbohydrate summary to the user 8, and may prompt the user to explain (if possible) certain values (e.g., abnormally high values or abnormally low values). For example, the high values may be attributed to eating out at a restaurant.

In another example, mHealth application 1 may display a weekly blood glucose and activity summary to the user 8. mHealth application 1 may determine that exercise on one day caused the user 8 to have a below target blood glucose event, and remind the user 8 to consume an amount (e.g., 15 grams) of carbohydrates before exercise to prevent hypoglycemia.

mHealth application 1 may determine a correlation between blood glucose scatter and testing frequency to determine an optimum testing frequency for a given user 8, which may provide health value to the user 8, economic value (e.g., by reducing extraneous test strips from being used), and reduce abuse, waste, and fraud. mHealth application 1 also may determine a correlation between blood glucose scatter and medication adherence.

Method 400 may return to step 414 after the plan is maintained or updated at step 428.

While steps 401-428 are depicted in a particular order, the principles of the present disclosure are not limited to the order depicted in FIG. 4.

Additional Examples

The treatment plan time period can be split into three separate phases: a first phase (e.g., an onboarding phase), a second phase (e.g., an intensive phase), and a third phase (e.g., a maintenance phase). The first phase may include a registration phase where the user 8 enters personal identifying information and initial patient data (e.g., as in step 401). The first phase may include a general introduction of a treatment plan, the goals of the plan, and/or a weekly challenge (or first weekly goal). In one example, the first phase may extend for a minimum of two weeks (e.g., weeks one and two of the treatment plan). The second phase follows the first phase. At the conclusion of the first phase, a user 8 is determined to be either in-target or out-of-target with respect to the treatment plan. In-target may mean that the user 8 fulfills values for each assigned parameter (e.g., blood glucose), and if the user 8 is not in target, they may be considered out of target (e.g., blood glucose levels are too high or too low). During the second phase, the user 8 may be presented different treatment plans based on whether the user 8 is determined to be in-target or out-of-target. In one example, the second phase may extend for a minimum of two weeks (e.g., weeks three and four of the treatment plan). At weekly intervals during, and at the conclusion of, the second phase, the user 8 is determined to be either in-target or out-of-target. If the user 8 is determined to be in-target at the conclusion of the second phase, the user transitions to the third phase of the treatment plan. If the user 8 is determined to be out-of-target at the conclusion of the second phase, the user 8 remains in the second phase until the user 8 is determined to be in-target, in which the user transitions to the third phase. If at any point the user transitions from in-target to out-of-target while in the third phase, the user 8 may return to the second phase of the treatment plan.

Treatment plans may be presented to patients or users in phases in order to increase compliance with the plan, for example, by making compliance with the treatment plan easier when the plan is initiated. Then, based on the user 8 reaching certain compliance thresholds, the plan may become more complex and capture additional data points, allowing for the treatment to be more robust.

Figure 5:
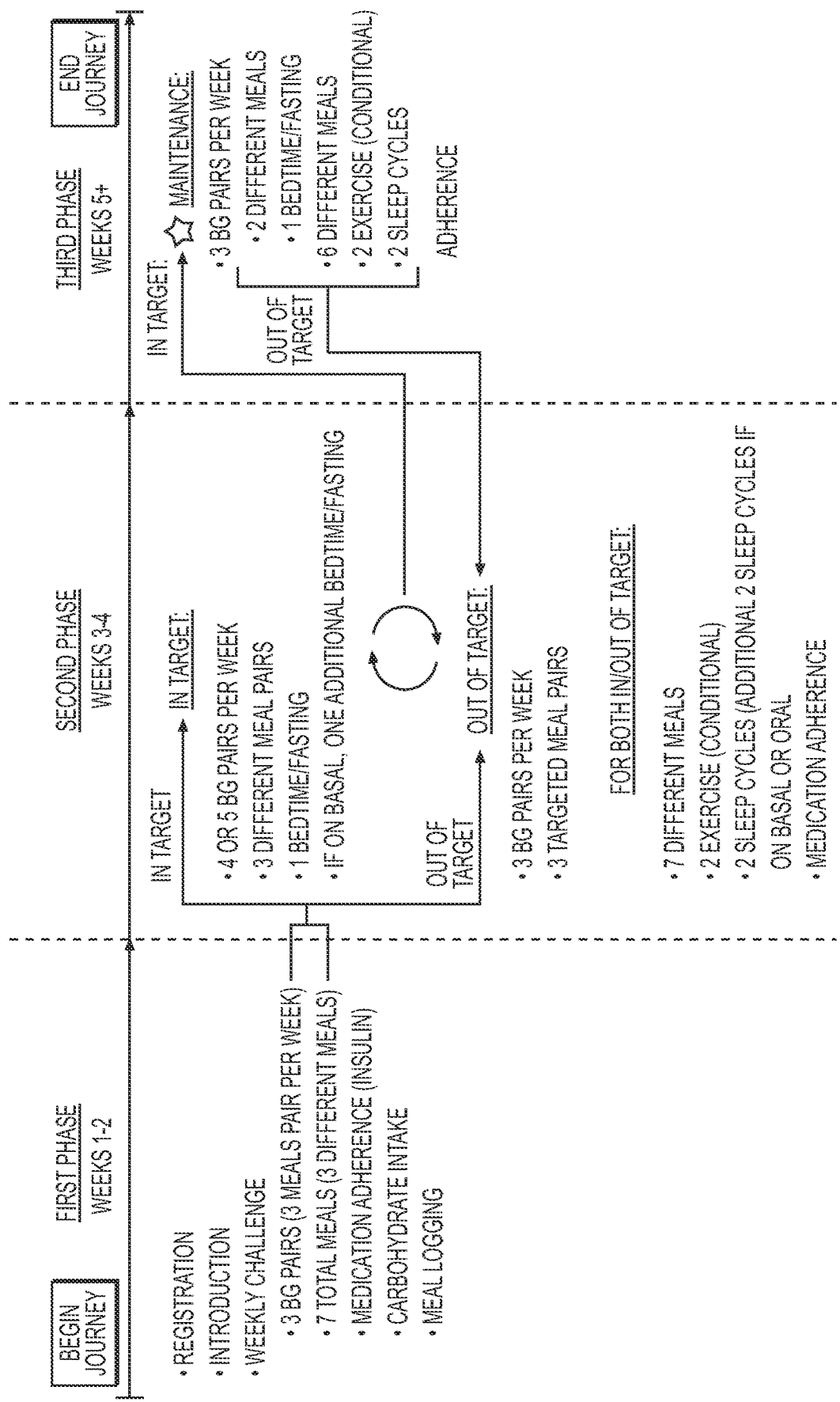
FIG. 5 is a flowchart of an exemplary method, according to another example of the present disclosure.

FIG. 5 is an example of a user 8 (e.g., patient, Yolanda) using a predictive and adaptive health management system according to the disclosure. Yolanda's treatment plan time period has been set to 12 weeks. The treatment plan time period may be longer or shorter. Yolanda is a 65 year-old, Caucasian female with type-2 diabetes, abnormally high A1C levels (7.0%), abnormally high blood glucose levels (150 mg/dL), and is overweight by 15 pounds. Her doctor has prescribed the software application to manage her type-2 diabetes and restore her abnormal A1C level, abnormal blood glucose level, and her weight to healthier levels. As described earlier above, a treatment plan time period is comprised of a first phase (e.g., an onboarding phase), a second phase (e.g., an intensive phase), and a third phase (e.g., a maintenance or ongoing phase). Per the example, during a first day of the first phase, Yolanda is required to input data into the application software—registering her name, her type-2 diabetes diagnosis, which is greater than six months. Yolanda also familiarizes herself with her first set of weekly challenges. Per the example, Yolanda adheres to a bolus insulin regimen. During her first phase (which comprises weeks one and two of the treatment plan time period), Yolanda will input into the software application of her device her blood glucose meal pair levels (at least three times), and track at least seven total meals including at least one tracking of a breakfast, a lunch, and a dinner. After the first phase is completed, mHealth application 1 will determine if Yolanda is in-target or out-of-target. During the second phase, or intensive phase (which extends at least weeks three and four of the treatment plan), Yolanda will be prescribed an in-target treatment plan comprising four or five BG pairs per week, including three different meal BG pairs, one bedtime/fasting BG pair; and one bedtime/fasting if also on a basal regimen. If at any point during the second phase, Yolanda falls out-of-target, she will be prescribed to an out-of-target treatment plan comprising three BG pairs per week comprising three targeted meal pairs. Further, during the second phase, as part of any treatment plan, Yolanda may be instructed to log seven different meals, two conditional exercise routines, two cycles of sleep (and an additional two cycles of sleep if she is on Basal or Oral insulin), and adhere to her originally prescribed medication regimen. If at the conclusion of the second phase, Yolanda is in-target, she may proceed to a third, maintenance phase. The third phase, in this example, may extend for eight weeks, corresponding to weeks 5-12 of the treatment plan. During the third phase of her treatment plan, Yolanda is prescribed a maintenance plan of three BG pairs per week comprising two different meal pairs and one bedtime/fasting pair. Yolanda also tracks six different meals, two conditional exercise routines, two cycles of sleep, and a medication during the third phase. If Yolanda falls out-of-target during the third phase, she may be assigned the out-of-target treatment plan from the second phase.

Figure 6:
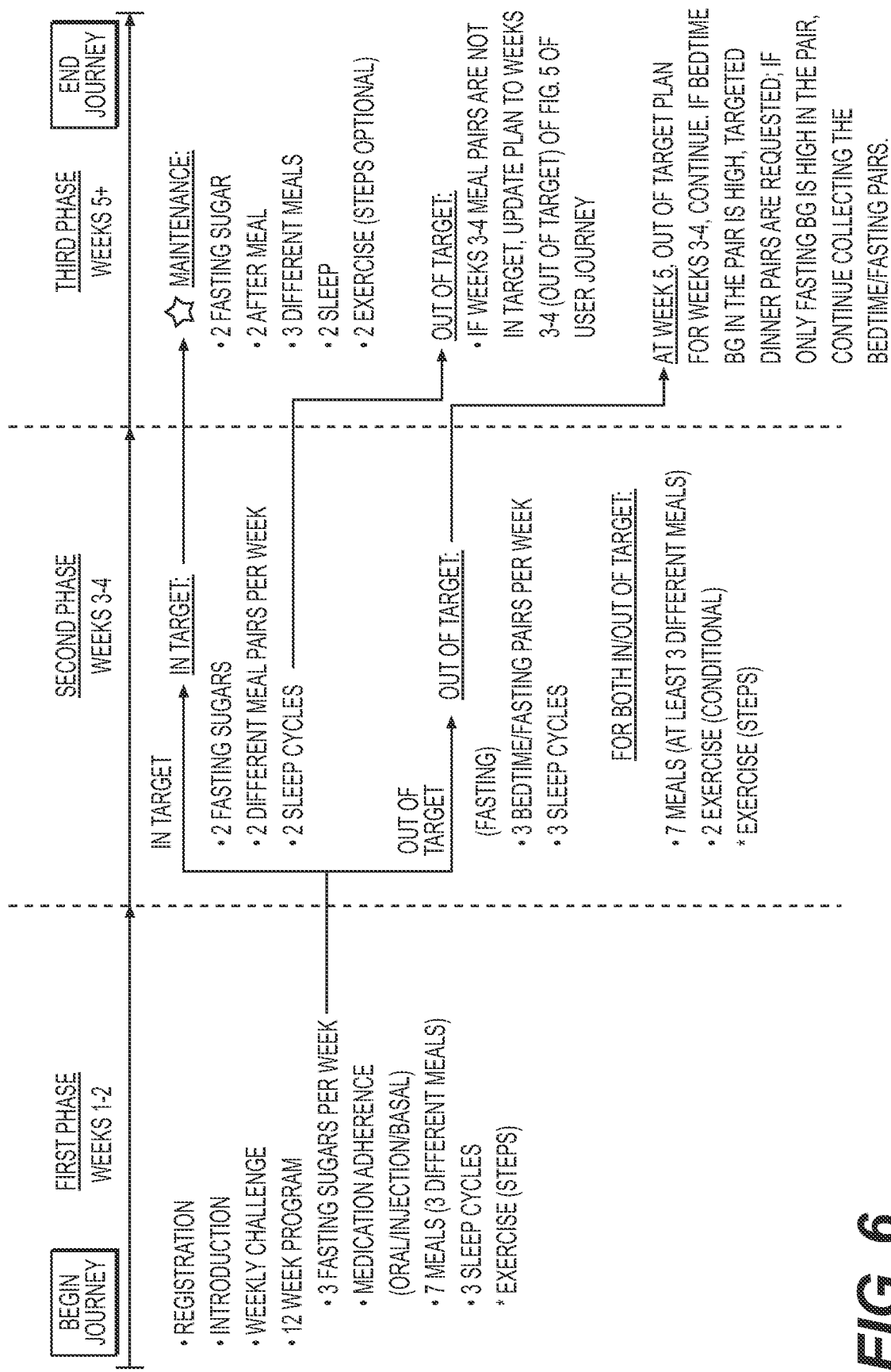
FIG. 6 is a flowchart of an exemplary method, according to another example of the present disclosure.

It is appreciated that for each week of the 12 weeks of Yolanda's treatment plan time period, she will be furnished a weekly summary of her results, including an assessment of her activities and whether she accomplished any of her goals relative to her treatment plan. After week 1 of the plan, Yolanda may fill out a questionnaire FIG. 6 is also an example of a user 8 (e.g., named Omkar) using the health management system of the disclosure. Omkar's treatment plan time period has been set to 12 weeks. Omkar is a 55 year-old, Indian-American male with type-2 diabetes, slightly above normal A1C levels (6.4%), slightly above normal fasting blood glucose levels (105 mg/dL), and uses tobacco (e.g., smokes a pack of cigarettes per day). Omkar was only recently diagnosed with type-2 diabetes (within the past six months). His doctor has prescribed the software application to manage his new diabetes diagnosis, and to restore his abnormal A1C level, abnormal blood glucose level, and try to encourage him to stop smoking. For purposes of conciseness, the steps of Omkar's user journey will reference, where applicable, the description above. Omkar may register and input data in a substantially similar manner as Yolanda above. Per the example, Omkar adheres to an oral insulin regimen. During his first phase (which lasts two weeks and comprise weeks one and two of the treatment plan time period), Omkar will input into the software application of his device three fasting sugars per week, medication adherence (oral/injection/Basal), seven meals, three sleep cycles, and the number of steps he takes daily. After the first phase is completed, Omkar may be determined to be in-target or out-of-target. During the second phase, or intensive phase (which lasts two weeks and comprises weeks three and four of the treatment plan), if Omkar is in-target, Omkar will be prescribed an in-target treatment plan comprising two fasting sugars, two different meal pairs per week, and two sleep cycles. If at any point during the second phase Omkar falls out-of-target, he will be prescribed an out-of-target plan comprising three bedtime/fasting pairs per week, and three sleep cycles. Regardless if Omkar is in-target or out-of-target during the two weeks of his second phase, his treatment plan will include logging at least seven different meals, two conditional exercise routines, and a daily minimum number of steps taken. If at the conclusion of the second phase, Omkar is in-target, he transitions into a third maintenance phase. The third phase, in this example, extends eight weeks, which correspond to weeks 5-12 of the treatment plan. During the third phase of his treatment plan, the maintenance plan comprises two fasting sugar, two after meal, three different meals, two sleep cycles, and two exercise routines, and steps daily.

In another example, mHealth application 1 may receive GPS data from the electronic device 19, and based on a time proximity to one or more scheduled meals of the treatment plan to be consumed by the user 8, may use the GPS data to identify restaurants in proximity to the user 8 and that are cataloged in a database. The database may include meals offered by the cataloged restaurants along with their carbohydrate content. mHealth application 1 may present a list of the catalogued restaurants to the user 8 via the electronic device, and the list may include recommended meal options at the identified restaurants based on the carbohydrate content of meals offered by the cataloged restaurants. mHealth application 1 then may receive a selection of a catalogued restaurant from the user 8, and generate a walking route for the user 8 to travel along from a current location of the user 8 to the selected restaurant.

In another example, mHealth application 1 may receive an indication from the user 8 that the user 8 would like to exercise, and, after receiving the indication from the user 8, retrieve GPS data from the electronic device 19. mHealth application 1 then may generate a route for the user 8 to walk or bike along, and a distance of the route may be based on exercise prescribed to the user 8 in the treatment plan. That is, the distance of the route may help the user 8 achieve a prescribed number of steps from the treatment plan.

In yet another example, mHealth application 1 may communicate with a watch (e.g., a smart watch) associated with the user 8. For example, the watch may display a last recorded blood glucose value of the user 8 along with the time that the recordation took place. The watch also may be used to remind a user 8 to perform one or more measurements, including, e.g., one or more measurements of a blood glucose pairing. For example, the watch may vibrate when the user 8 should perform a blood glucose measurement. When a low blood glucose value has been entered into mHealth application 1, the watch may enter a low blood glucose reminder state, in which the watch displays the last-recorded low blood glucose value with a timer for when a new blood glucose value should be entered. In some examples, a user 8 may enter information into mHealth application 1 via the smart watch.

Figure 7:
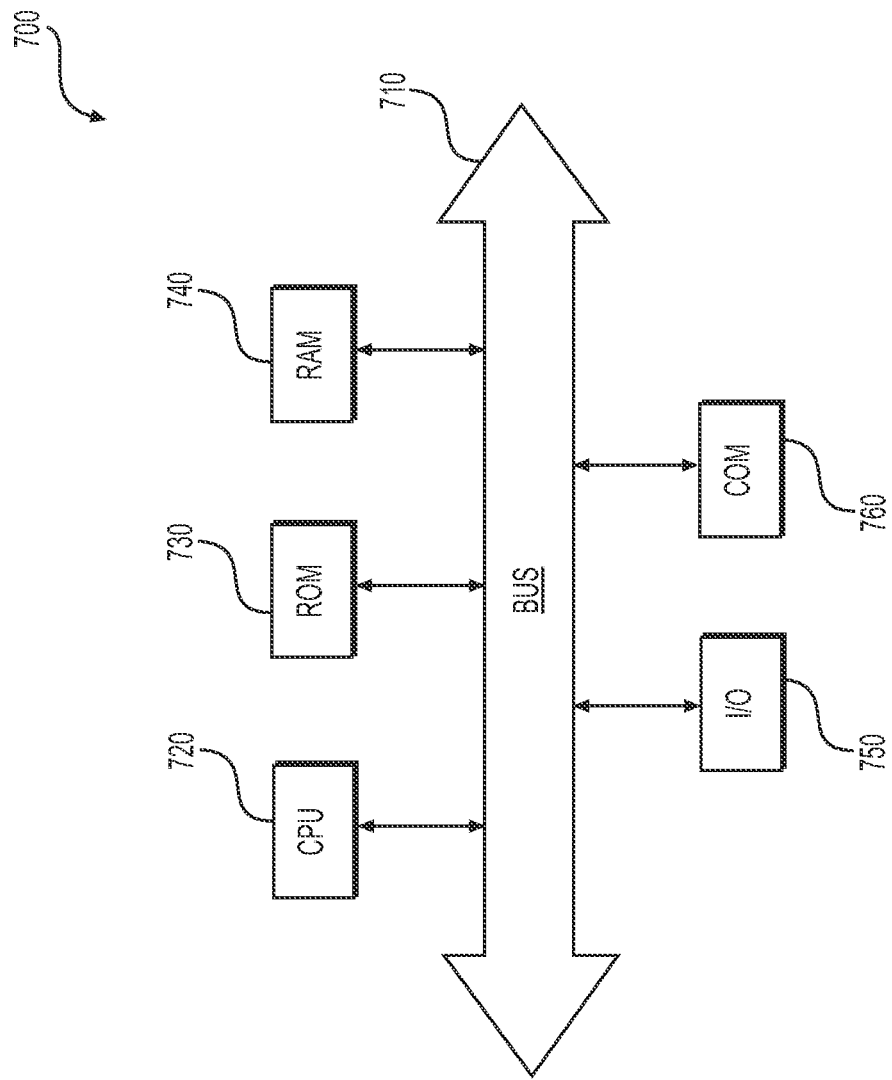
FIG. 7 is a simplified functional block diagram of a computer that may be configured as a host server, for example, to function as healthcare provider decision-making server, according to an example of the present disclosure.

FIG. 7 is a simplified functional block diagram of a computer that may be configured as a host server, for example, to function as healthcare provider decision-making server. FIG. 7 illustrates a network or host computer platform 700. It is believed that those skilled in the art are familiar with the structure, programming, and general operation of such computer equipment and as a result, the drawings should be self-explanatory.

A platform for a server 700 or the like, for example, may include a data communication interface for packet data communication 760. The platform also may include a central processing unit (CPU) 720, in the form of one or more processors, for executing program instructions. The platform typically includes an internal communication bus 710, program storage, and data storage for various data files to be processed and/or communicated by the platform such as ROM 730 and RAM 740 or the like. The hardware elements, operating systems, and programming languages of such equipment are conventional in nature, and it is presumed that those skilled in the art are adequately familiar therewith. The server 700 also may include input and output ports 750 to connect with input and output devices such as keyboards, mice, touchscreens, monitors, displays, etc., and communication ports 760. Of course, the various server functions may be implemented in a distributed fashion on a number of similar platforms to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Various examples of the present disclosure may utilize continuous glucose monitoring (CGM) devices or self-monitoring of blood glucose (SMBG) devices to collect blood glucose levels of user 8. A CGM device may include a small sensor placed subcutaneously in the user 8. A transmitter on the CGM device may send measured information to a wireless device, such as, e.g., an electronic device 19 described above with reference to FIG. 1. Communication between the CGM device and electronic device 19 may be by any suitable wireless protocol, such as, e.g., Bluetooth, RF, or the like.

Figure 8:
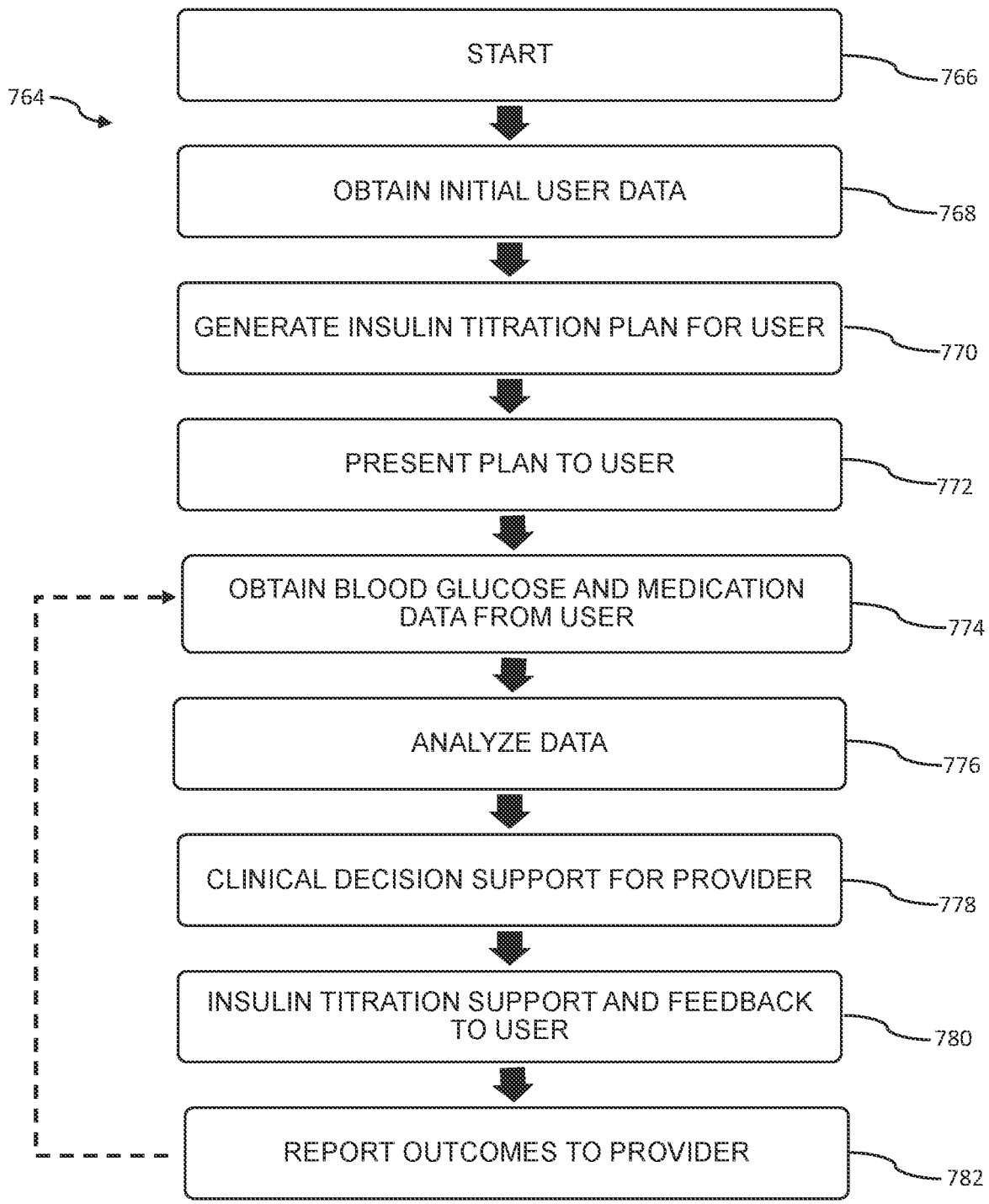
FIG. 8 is a flowchart of an exemplary method, in accordance with an example of the present disclosure.

FIG. 8 displays a flow diagram of an exemplary method 764 starting at a step 766 for providing insulin titration recommendations and support to a user of mHealth application 1. As shown in FIG. 8, at step 768, electronic device 19 and/or server 29 may obtain initial data from a user before generating an insulin titration plan. The user may enter the data into the electronic device 19, which may be sent to server 29. Step 768 may be substantially similar to step 401 of FIG. 4.

Using the data collected at step 768, mHealth application 1 may generate an insulin titration plan for the user (step 770). The generated insulin titration plan 770 may include an insulin titration algorithm to optimize the user's insulin dosage. A titration algorithm may include a starting dosage amount of insulin, an increment that the dosage amount is increased after a set period of time, requirements for the user to test blood glucose levels at specific times of day, or instructions for the user to use a specific brand or types of insulin or other medication for treatment. The titration algorithm may further include a start date for the user, a target average blood glucose level for the user to achieve, or any other target value for the user's test results. The titration algorithm may include an algorithm intended for basal insulin, bolus insulin, pre-mixed insulin or any combination thereof. In one embodiment, a titration algorithm may include a basal insulin regimen requiring one blood glucose measurement daily for three days to titrate the proper insulin dosage. In another embodiment, a titration algorithm may include a premixed insulin regimen requiring two blood glucose tests daily for three days. In another embodiment, a titration algorithm may include a basal plus bolus insulin regimen that may require four blood glucose tests daily for one week.

In one example, the insulin titration plan generated in step 770 may include Lantus®, Levemir®, or Neutral Protamine Hagedorn (NPH) as the brand or type of insulin prescribed to the user. An algorithm for basal insulin titration may be used and may require the user to conduct a daily fasting blood glucose test. The cycle length of the insulin titration plan may be every one, two, three, four, or any other number of days or may be for any number of fasting blood glucose tests recorded. The titration plan may include treatment with basal insulin alone, basal plus insulin, basal-bolus insulin, or any combination thereof. The titration algorithm may instruct the user to stop titration when the user fails to enter a certain number of consecutive fasting blood glucose tests, when the user's blood glucose is below 70 mg/dL, or if the user reports a symptom of hypoglycemia or hyperglycemia. Symptoms of hypoglycemia may be the user reporting symptoms of hunger, dizziness, shakiness, weakness, drowsiness, rapid hearbeat, clamminess, paleness, irritability, sudden changes in mood, sweating, or unconsciousness. Symptoms of hyperglycemia may include frequent urination, weight loss, increased thirst or increased sugar levels in urine.

In another example, the insulin titration plan generated in step 770 may include Humalog®, Novolog®, or Apidra® as the brand or type of insulin prescribed to the user. An algorithm for bolus insulin titration may be used and may require the user to conduct a blood glucose test after each main meal ("post-main meal") or immediately after all meals at which insulin is dosed. A "main meal" may be the largest meal the user eats in a twenty-four hour period, may be the user's first, second, third, or fourth meal of the day, or any other meal. The cycle length of the insulin titration plan may be every one, two, three, four, or any other number of days and after at least three days of blood glucose tests are entered into mHealth application 1 by the user or otherwise received by mHealth application 1. In this example, the insulin titration algorithm may be combined with a basal insulin titration algorithm to reach the insulin titration plan. The titration algorithm may instruct the user to stop titration when the user fails to enter three consecutive post-meal blood glucose tests on any of the final three days of the titration cycle, when the user's blood glucose is below 70 mg/dL, or when the user reported a symptom of hypoglycemia or hyperglycemia.

In another example, the insulin titration plan generated in step 770 may include Humalog® Mix 75/25™ or Novolog® Mix 70/30 as the brand or type of insulin prescribed to the user. An algorithm for pre-mixed insulin may be used and the algorithm may require the user to conduct two blood glucose tests daily. The titration cycle may be any number of days and at least after three consecutive days of blood glucose tests are entered into mHealth application 1 by the user or otherwise received by mHealth application 1. In some instances, no other insulin titration algorithms may be combined with this insulin titration algorithm. The titration algorithm may instruct the user to stop titration when the user fails to enter at least two blood glucose test results daily on the final three days of the titration cycle, when the user's blood glucose is below 70 mg/dL, or when the user reported a symptom of hypoglycemia.

Once an insulin titration plan is generated, mHealth application 1 presents the plan to the user via electronic device 19 (step 772) or the user's provider may present the plan to the user.

Next, at step 774, mHealth application 1 may receive data relating to the insulin titration plan. The data may be manually input by the user via electronic device 19 or automatically generated or detected by mHealth application 1, and may include any of the data received at step 418 of FIG. 4.

Next, at a step 776, data from the user, which is stored on the server 29, may be analyzed, e.g., by one or more machine learning algorithms and/or by any suitable processor. mHealth application 1 may determine whether the user's blood glucose test results or average blood glucose is within a specific target range. mHealth application 1 may determine whether the user is exhibiting signs of hypoglycemia or hyperglycemia. mHealth application 1 may determine a recommended dosage increase or decrease based on the user's test results, such as an increase in insulin dosage or increase in the increment used to increase medication during titration. Also, mHealth application 1 may determine compliance of the user with each prescribed activity (e.g., one or more of the activities described previously, including blood glucose monitoring, titration of insulin, etc.). mHealth application 1 may determine when a user administered a dose of insulin which deviates from the prescribed dose provided in the insulin titration plan. mHealth application 1 may adjust the user's treatment and/or titration plan based on the user's average blood glucose, compliance with each prescribed activity, or other suitable aspect of the original goal and/or plan. In an example, adherence to a user's titration regimen can be analyzed to determine if the user is not compliant with the prescribed regimen of the user's original titration plan. mHealth application 1 may determine a user's compliance to each aspect of the titration plan, such as, e.g., proper increase in medication (e.g., increases in insulin), adequate blood glucose testing frequency, or adequate timing of blood glucose testing (e.g., after a main-meal, etc.).

In step 776, for example, any of the algorithms discussed herein may be applied to the data to learn and otherwise extract information from the data, such as for use in identifying low or high average blood glucose test results, identifying user errors in titration regimens and/or user behavioral patterns. The results of any such algorithms may be reported to the user's provider, stored in mHealth application 1 or an outside server, or reported to another health care provider outside of the user's provider.

In step 778, the user's blood glucose test results, any other test results, and data analysis performed by mHealth application 1 may be reported to the user's provider during the insulin titration regimen. The feedback provided to the user's provider in step 778 allows the provider to adjust the user's titration regimen based on real-time testing results from the user. The user's provider may increase or decrease dosages of medication, may adjust the timing for when user takes medication, adjust the timing of the user's blood glucose testing, or otherwise adjust the titration regimen. For example, if user's blood glucose shifts outside of the expected results at a specific dosage, the user's provider may update the titration regimen and send the user a message via mHealth application 1 (step 780). In another example, the user's provider may alert the user to make an appointment to see the provider.

Titration may be completed if the administered dose of basal insulin is exactly the prescribed dose according to the algorithm, or is within a prescribed range. Titration may be halted at 60 units of insulin, in which case medical provider may need to split the dose of insulin or add bolus insulin, although other suitable values are also contemplated. Titration may occur over a period of six months, although other time periods shorter and longer are contemplated. Once an acceptable dosage is achieved, the medical provider may receive a report. The titration function of mHealth application 1 may monitor the user's blood glucose values for an additional time period, e.g., six months after titration. If the blood glucose averages go above-target by, e.g., 10 mg/dL, re-titration commences.

In another example, mHealth application 1 may identify that in the past week, the user displayed a pattern of low fasting blood sugar despite regular insulin titration. In this example, mHealth application 1 may determine that the user's hypoglycemia is most likely due to the type of insulin prescribed to the user, and that because the low morning readings have persisted, that the user should contact his or her provider to adjust his or her insulin titration regimen. In addition, mHealth application 1 may report this message to user's provider (step 782).

In one example, a user may be directed by a physician to self-titrate their insulin dosage by increasing five dosage units every three days if their blood glucose level has not reached their target average glucose level. While following this titration algorithm of increasing five dosage units every three days, the user may have an average fasting blood glucose that is on target, but the user's post dinner blood glucose may be elevated. mHealth application 1 may advise the user to titrate the user's insulin dosage, from five units to eight units administered post dinner, to help prevent the user's post meal blood glucose from elevating. mHealth application 1 may then report the outcomes of the insulin titration to the user's provider.

In another example, the mHealth application 1 may report to the user's provider the following message: "Your patient Mrs. Smith is now using insulin at 8 units administered post dinner. The average post dinner blood glucose went from 245 mg/dL at baseline to 175 mg/dL. There was no hypoglycemia reported." In response to reports, the user's provider may adjust the user's recommended insulin dosage in mHealth application 1. Different titration algorithms may be stored in a database associated with mHealth application 1, and depending on the type of insulin used (e.g., basal insulin, fast-acting insulin, pre-mixed insulin, or dosing-type insulin) each algorithm may require a certain number of blood glucose tests per day or insulin dosages per day. When mHealth application 1 is used to assist with a user's insulin titration, "titration" messages may be sent to electronic device 19 to give the user titration instructions.

An example titration message generated by mHealth application 1 and sent to electronic device 19 may read as follows: "Hi Dev, Your health care provider has prescribed you a type of insulin called Levemir. It is a long-acting insulin also called basal insulin. The purpose of this insulin is to get your fasting blood glucose into the target range of 70-130 mg/dL. Your health care provider wants to adjust the dose of Levemir every 3 days depending on your fasting blood glucose readings. Your current fasting blood glucose reading is 185 mg/dL. Your dose of Levemir is 15 units every day. If you enter your fasting or before breakfast blood glucose every day for the next 3 days, we will remind you if you need to adjust your Levemir dose according to the treatment plan."

Another example of a titration message generated by mHealth application 1 to assist a user with insulin titration may include the following: "Hi Dev, Your fasting or before breakfast blood glucose for the past 3 days were 187, 201, and 175 mg/dL, which averages to 188 mg/dL, which is above target. According to your health care provider's plan, today you should increase the dose of the Levemir from 15 units every evening to 18 units every evening. If you enter your fasting or before breakfast blood glucose every day for the next 3 days, we will remind you if you need to adjust your Levemir dose according to the treatment plan."

Another example of a titration message generated by mHealth application 1 to assist a user with insulin titration may include the following: "Hi Dev, We haven't seen a fasting or before breakfast blood glucose from you in the past day. If you enter your fasting or before breakfast blood glucose every day for the next 3 days, we will remind you if you need to adjust your Levemir dose according to the treatment plan." mHealth application 1 may be programmed to repeatedly send this or similar reminder messages to the user and notify the user's provider after a certain number of reminder messages have been sent.

Another example of an insulin dosing message generated by mHealth application 1 to assist a user with insulin titration may include the following: "Hi Dev, Because of the hypoglycemia you had earlier today, you should reduce your Lantus dose to 43 units. No further increase in the dose will be suggested until you see your health care provider."

In some embodiments, once an optimal dosage level is achieved through insulin titration, mHealth application 1 will send a report to the health care provider. The report may be transmitted electronically or may be automated once a specific blood glucose average is reached or other threshold testing result is met. In some embodiments, if the blood glucose average exceeds the target blood glucose average by 10 mg/dL or any other threshold average set by the user's provider, re-titration may commence.

In some embodiments, mHealth application 1 may instruct the user to halt insulin titration and the patient's health care provider may be alerted when a user reports symptoms of hypoglycemia even if the user's blood glucose levels are normal. mHealth application 1 may generate messages to alert the user of the symptoms of hypoglycemia.

Figure 9:
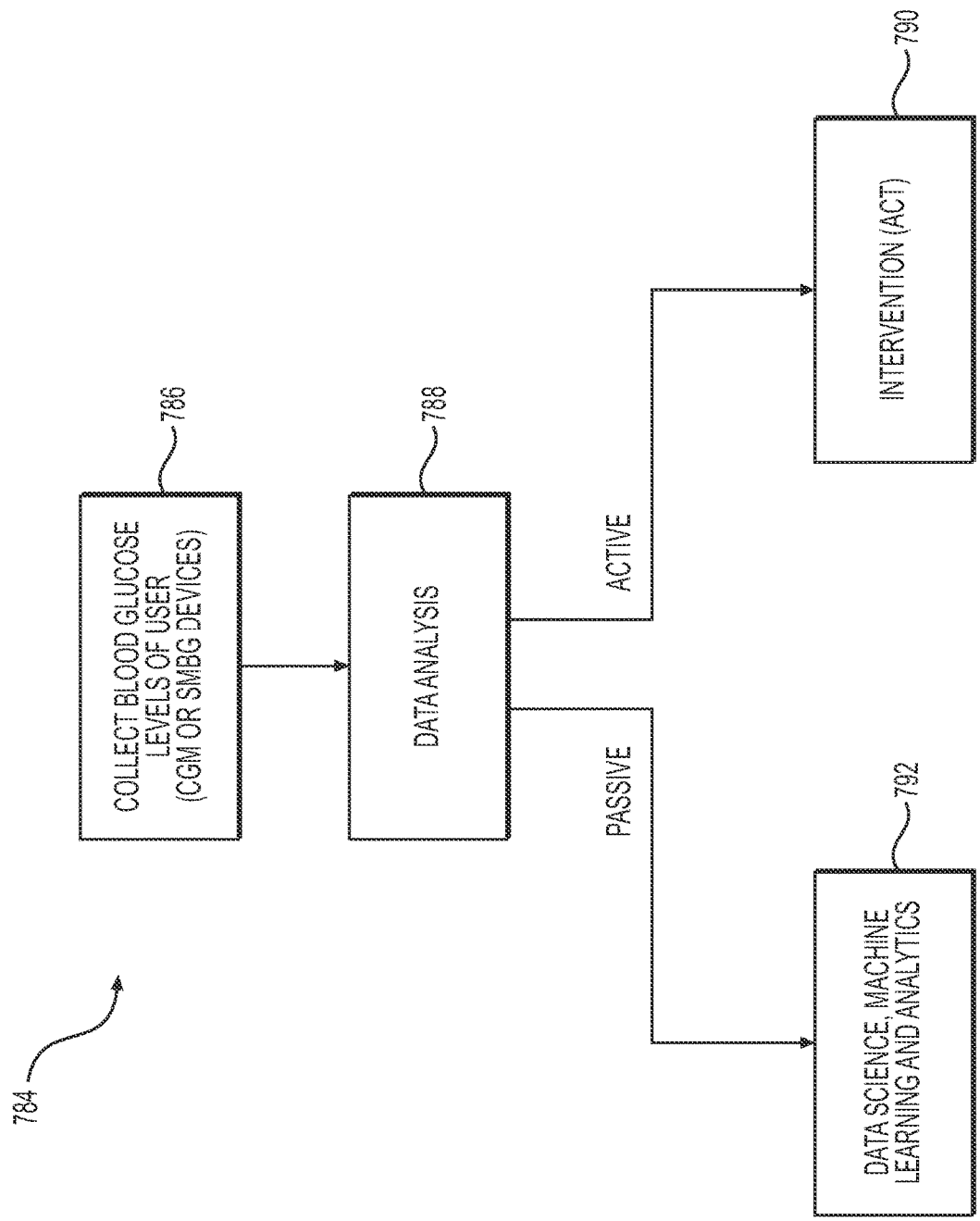
FIG. 9 is a flowchart of an additional exemplary method, in accordance with an example of the present disclosure.

FIG. 9 shows an exemplary method 784. Method 784 may begin at step 786, where electronic device 19 may receive data including blood glucose levels of user 8 measured by a CGM or SMBG device. The data may be received continuously by electronic device 19 from CGM or SMBG device, or CGM or SMBG device and electronic device 19 may sync at certain time intervals (e.g., every 5 minutes). After collecting the data at step 786, method 784 may proceed to step 788, where data analysis substantially similar to other data analysis described herein, may be performed.

Method 784 may proceed to step 790, where the data may be used to provide real-time feedback based on, e.g., discrete blood glucose values, or a direction and rate of change of blood glucose values. That is, mHealth application 1 may be configured to provide interventions and/or educational messages to user 8 based on high or low blood glucose values that may have otherwise been unidentified when user 8 utilizes only self-monitoring techniques.

Figure 10:
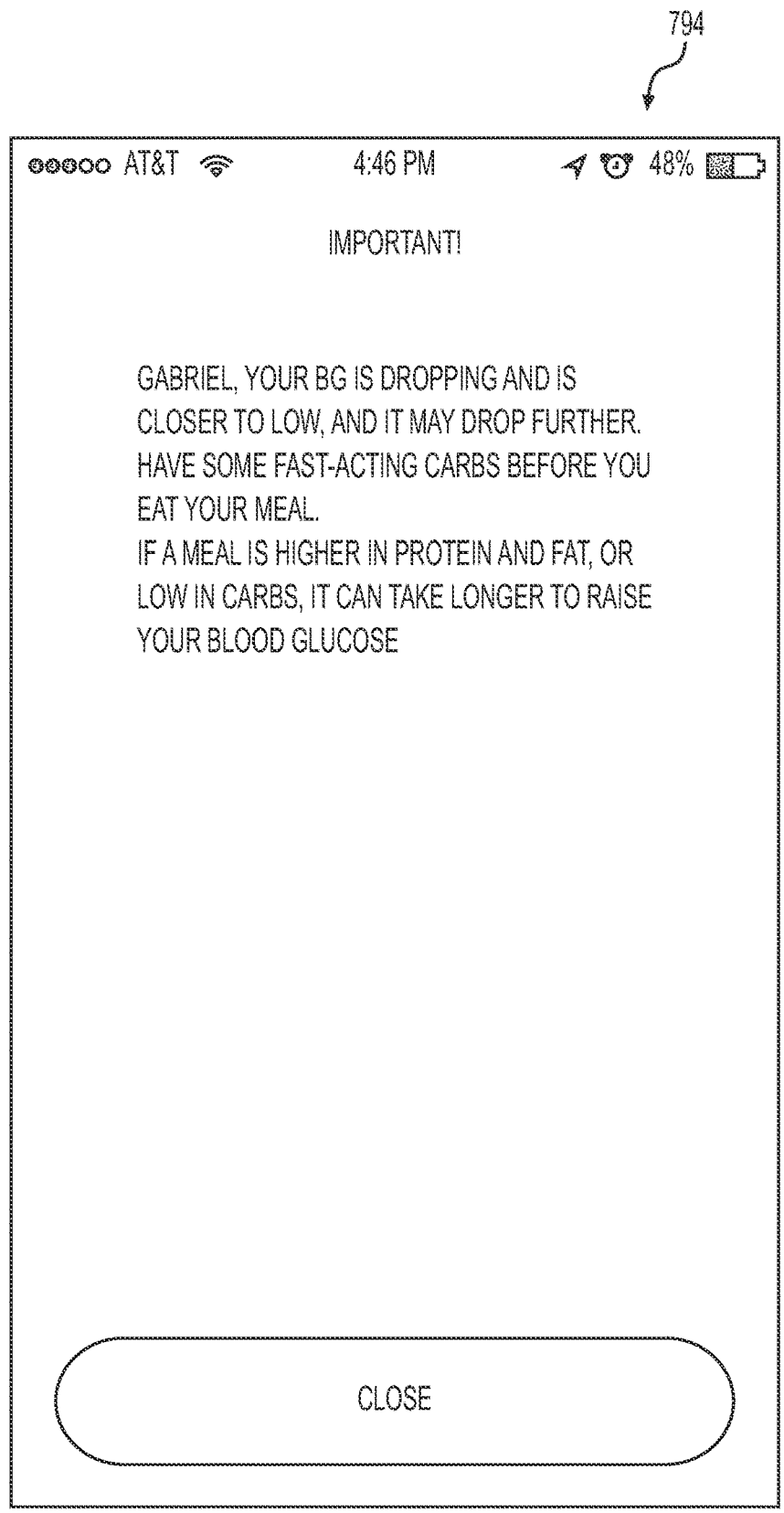
FIG. 10 is a screenshot of an exemplary message, in accordance with an example of the present disclosure.

FIG. 10 shows an exemplary screenshot of a message generated by mHealth application 1. Referring to FIG. 10, mHealth application 1 may provide a notification 794 to user 8 that BG levels are approaching or have reached a low, hypoglycemic range, and that user 8 should consume fast-acting carbohydrates before a next meal. mHealth application 1 also may provide other messages to user 8, such as, e.g., potential causes of the measured values. In an example where a low blood sugar is detected, mHealth application 1 may inform user 8 that meals high in protein and fat, or low in carbohydrates, may take longer to raise blood glucose levels. Thus, an intervention at step 790 may include instructing the user to consume an amount of carbohydrates, e.g., 30 grams of fast-acting carbohydrates, and that user 8 should re-check blood glucose levels after a time interval. In some examples, the time interval may be 15 minutes after the instruction to consume fast-carbohydrates is delivered to the user. A countdown timer may be displayed via mHealth application 1. mHealth application 1 may be configured to disable certain features of electronic device 19 until a blood glucose level measured by a CGM device is out of the hypoglycemic range, or into a normal range. In other examples, mHealth application 1 may accept a manual entry of blood glucose values to determine that user 8 is no longer in the hypoglycemic range, or is back into the normal range.

Step 790 also may include providing an intervention to user 8 based on a direction and/or rate of change of blood glucose values. For example, mHealth application 1 may notify user 8 that blood glucose levels are trending downward or upward, and may provide an intervention based on a projected high value or a projected low value based on the direction and rate of change. In other examples, mHealth application 1 may not provide any intervention, but may provide feedback based on the detected trend.

FIG. 11 shows two screenshots generated by mHealth application 1. In screenshot 796, mHealth application 1 shows that a downward trend of blood glucose values has been detected, but that based on a last bolus insulin delivery, the blood glucose values of user 8 are expected to remain in the target range. In screenshot 798, mHealth application 1 shows an upward trend of blood glucose. However, mHealth application 1 may determine that a most recent bolus insulin delivery has not exhibited a maximal effect, and may recommend that correctional insulin is not required. In other examples, mHealth application 1 may determine, based on the direction and rate of change of blood glucose values, that a hypoglycemic event or a hyperglycemic event is likely to occur, and may suggest that user 8 take corrective action, such as, e.g., consuming an amount of fast-acting carbohydrates or administering a corrective insulin dose. When severe and/or life-threatening events are predicted, mHealth application 1 may initiate communication with a health care provider and/or emergency response personnel.

Method 784 also may provide non-real-time, or delayed feedback, based on received data from a CGM or SMBG device. That is, a delay of, e.g., at least four hours, may elapse before feedback based on data from CGM or SMBG device is provided to user 8.

Figure 12:
FIG. 12 is two screenshots of two exemplary messages, in accordance with an example of the present disclosure.

FIG. 12 shows two exemplary screenshots generated by mHealth application 1. Screenshot 800 in FIG. 12 shows exemplary delayed feedback that may be provided by mHealth application 1. Screenshot 800 illustrates an example where mHealth application 1 detected an extreme downward rate of change in blood glucose values of user 8 from 230 mg/dL to 65 mg/dL in one minute. mHealth application 1 may provide an educational message to user 8 based on the detected event, for example, informing user 8 that extreme drops in blood glucose value can be dangerous. mHealth application 1 also may determine a cause of the extreme rate of change, such as, e.g., that user 8 consumed an improper dose of insulin before a meal. Screenshot 802 illustrates an example where mHealth application 1 detected high blood glucose values during the day despite user 8 having in target values in the early morning.

Referring to FIG. 9, at step 792, the data received from a CGM or SMBG device also may be used passively to identify patterns between the continuous blood glucose values and other data sets received by mHealth application 1, such as, e.g., timing and amounts of carbohydrates consumed, timing an amounts of medication consumed, exercise performed, sleep, time of day, day of week, stress level, or any other suitable data set. mHealth application 1 may use the identified patterns to determine trigger events that lead to undesirable patterns of blood glucose values or undesirable rates of change of blood glucose values. The identification of and subsequent detection of trigger events based on data received from a CGM or SMBG device may be substantially similar to the mechanisms described above with respect to method 400 and FIG. 4.

In one example, mHealth application 1 may assist with determining a medication dosage or regimen for a user, e.g. a patient. In one example, mHealth application 1 may assist a provider with determining a patient's required insulin dosage. mHealth application 1 may assist providers with counseling patients about the recognition, prevention and treatment of hypoglycemia. In an example where the user has diabetes, mHealth application 1 may guide the user to adjust the user's insulin dosage in order to optimize the user's average blood glucose level. mHealth application 1 may assist with titration of a user's medication in order to achieve an optimal dosage of the medication. mHealth application 1 may provide feedback to a user during titration of medication in order to achieve an optimal dosage of the medication, such as instructing the user to increase the dosage periodically until a desired level of blood glucose is achieved. Users may self-titrate their dose of medication when instructed to do so by their provider, and mHealth application 1 may assist with the user's self-titration by monitoring user's blood glucose levels and alerting the user and the provider when the user's blood glucose levels go outside an acceptable range during insulin titration. mHealth application 1 may recommend a change in type or timing of insulin administration if glycemic targets are not being reached at current insulin dosage levels.

In one example, mHealth application 1 may provide a comprehensive intervention service to the user while self-titrating a particular medication. mHealth application 1 may analyze a blood glucose test conducted by the user, and entered into mHealth application 1 by the user. The blood glucose test conducted by the user may be a SMBG test. In an alternative embodiment, mHealth application 1 may conduct a blood glucose test automatically or via a device coupled to the user to obtain the user's current blood glucose level. mHealth application 1 may adjust the insulin dosage for the user based on the patient's blood glucose test results entered into the application by the user. mHealth application 1 may send alert messages to the user's provider after blood glucose test results are entered into the application or may compile the blood glucose test results and send a periodic report of the results to the provider. The user's provider may adjust the user's recommended insulin dosage or titration increment in mHealth application 1. Alternatively, mHealth application may adjust the dosage or titration increment itself. Once a user's insulin dosage has been adjusted based on current blood glucose test results, the user may receive an alert message to adjust their insulin dosage. User alert messages may be received through electronic device 19. In some embodiments, a titration algorithm may be used by mHealth application 1 to calculate the proper insulin dosage based on the user's blood glucose test results. The user's provider, or mHealth application 1 itself, may alter or stop insulin titration during the titration regimen based on user's test results, and send user alert messages including instructions to alter or stop titration.

Proper insulin titration may improve blood glucose levels, and decrease over-utilization of health resources. This should result in cost savings for payers (e.g., insurance companies). Health care providers may value insulin titration through a mobile application because patients may achieve glycemic targets with fewer visits and phone calls. Patients and users may feel empowered to adjust their insulin dose and improve their blood glucose levels, further increasing engagement with mHealth application 1.

It would also be apparent to one of skill in the relevant art that the present disclosure, as described herein, can be implemented in many different examples of software, hardware, firmware, and/or the entities illustrated in the figures. Any actual software code with the specialized control of hardware to implement examples is not limiting of the detailed description. Thus, the operational behavior of examples will be described with the understanding that modifications and variations of the examples are possible, given the level of detail presented herein.

It is to be understood that both the foregoing general description and the following detailed description are exemplary and explanatory only and are not restrictive of the disclosed examples, as claimed.

Other examples of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for managing blood glucose levels of a user, the method comprising:

causing a continuous glucose monitoring device comprising a subcutaneous sensor, in the user, the continuous glucose monitoring device configured to provide blood glucose values of the user;

electronically receiving, at a server, using one or more processors, data including a length of time that the user has been diagnosed with a blood glucose condition, types and dosages of medications consumed by the user, and the blood glucose values of the user;

storing, using the one or more processors, the received data in a database connected to the one or more processors;

extracting health data, using the one or more processors, from the stored data, the health data comprising cohort data from one or more other health devices corresponding to one or more other users, the cohort data comprising blood glucose values of the one or more other user;

inputting, using the one or more processors, the health data into one or more machine learning algorithms to generate a treatment plan for improving the blood glucose values of the user at an end of a treatment period, as compared to blood glucose values of the user at a beginning of the treatment period, the treatment plan for the user to achieve a goal based on the length of time that the user has been diagnosed with the blood glucose condition, and the types and dosages of medications consumed by the user, wherein the treatment plan includes instructions for tasks to be performed by the user during a first subset of the treatment period, wherein the tasks include one or more of prescribed blood glucose measurement pairs to be measured before and after meals, prescribed timing and dosage of medication to be consumed by the user, a prescribed amount of carbohydrates to be consumed by the user, or prescribed exercise for the user to perform, wherein the one or more machine learning algorithms include one or more of artificial neural networks, Bayesian statistics, case-based reason, decision trees, inductive logic processing, Gaussian process regression, Gene expression programming, Logistic model trees, stochastic modeling, or statistical modeling;

verifying access rights of an electronic device of the user, wherein the verifying comprises compliance with at least one of a Health Insurance Portability and Accountability Act (HIPAA) privacy regulation, a legal regulation, a healthcare regulation, a user account, as an intended device, or a financial regulation;

outputting the generated treatment plan, using the one or more processors, to the user via the electronic device of the user;

electronically receiving, using the one or more processors, data relating to the treatment plan during the first subset of the treatment period, the data relating to the treatment plan including medications consumed by the user, amount of exercise performed by the user, and blood glucose levels of the user;

revising the treatment plan, using the one or more processors, for a subsequent subset of the treatment period based on a determined medication compliance, a determined exercise compliance, and identified patterns;

outputting the revised treatment plan to the user, using the one or more processors, via the electronic device, wherein the revised treatment plan includes one or more tasks to be performed by the user during the subsequent subset of the treatment period, wherein the tasks include a change in the one or more of the prescribed blood glucose measurement pairs to be measured before and after meals, the prescribed timing and dosage of medication to be consumed by the user, the prescribed amount of carbohydrates for the user to consume, or the prescribed exercise for the user to perform;

determining, using the one or more processors, based on the identified patterns, a trigger event that occurs before an adverse effect, the trigger event corresponding to deviation from an expected pattern; and sending a notification to the user, using the one or more processors, via the electronic device of the user upon detecting an instance of the trigger event, wherein the notification includes an identification of the trigger event to the user and an identification of the adverse effect.

2. The method of claim 1, wherein the machine learning algorithms generate the treatment plan based at least on the cohort data.

3. The method of claim 2, wherein the cohort data is further generated based on one or more individuals having one or more similarities with the user, the one or more similarities comprising a physical condition, a medical condition, and a psycho-determinant condition.

4. The method of claim 2, wherein the cohort data is generated based on one or more individuals that match a demographic of the user.

5. The method of claim 4, wherein the demographic is one or more of an ethnicity, a gender, an age range, a height, and a weight.

6. The method of claim 2, wherein the cohort data is based on one or more individuals each having a successful treatment plan for a medical condition shared by the user and the one or more individuals.

7. The method of claim 1, further comprising:

receiving, using the one or more processors, global positioning system (GPS) data from the electronic device of the user;

identifying, using the one or more processors, and based on the received GPS data and a time proximity to one or more scheduled meals of the treatment plan to be consumed by the user, restaurants in proximity to the user and that are cataloged in a database, wherein the restaurant database includes meals offered by the cataloged restaurants and a carbohydrate content of each meal;

outputting a list of the identified restaurants, using the one or more processors, to the electronic device of the user, wherein the list includes recommended meals, of the meals offered at the identified restaurants, based on the carbohydrate content of the meals offered by the identified restaurants;

receiving, using the one or more processors, a selection of a catalogued restaurant, of the output list of the identified restaurants, from the user; and generating, using the one or more processors, a walking route for the user to travel along from a current location of the user to the selected restaurant.

8. The method of claim 1, further comprising:

applying, using the one or more processors, the one or more machine learning algorithms to the received data relating to the treatment plan to determine a medication compliance by comparing types, timing, and dosages of medication to the prescribed types, timing, and dosages of medication, to determine a diet compliance by comparing a received amounts of carbohydrates consumed to the prescribed amounts of carbohydrates to be consumed, and to determine an exercise compliance by comparing the received amounts of exercise performed to the prescribed amounts of exercise to be performed.

9. The method of claim 1, further comprising:

applying, using the one or more processors, the one or more machine learning algorithms to the received data relating to the treatment plan to analyze types, timing, and dosages of medications consumed by the user, amounts of carbohydrates consumed by the user, amount of sleep of the user, the amount of exercise performed by the user, and the blood glucose levels of the user to identify patterns between the types, timing, and dosages of medications consumed by the user, the amounts of carbohydrates consumed by the user, the amount of sleep of the user, the amount of exercise performed by the user, and the blood glucose levels of the user.

10. A system for managing blood glucose levels of a user, the system comprising:

a memory having processor-readable instructions stored therein; and a processor configured to access the memory and execute the processor-readable instructions, which, when executed by the processor configures the processor to perform a method, the method comprising:

electronically receiving at a server, using one or more processor, before generation of a treatment plan, data including types and dosages of medications consumed by the user, and A1C values of the user;

storing, using the one or more processors, the received data in a database connected to the one or more processors;

extracting metadata, using the one or more processors, from the stored data;

inputting, using the one or more processors, the metadata into one or more machine learning algorithms to generate (a) a goal for the user, wherein the goal includes a reduction in the A1C value of the user at an end of a treatment period, as compared to an A1C value of the user at a beginning of the treatment period, and wherein the machine learning algorithms generate the goal based at least on cohort data for a cohort associated with the user and (b) the treatment plan for the user to achieve the goal is based on the types and dosages of medications consumed by the user, wherein the treatment plan includes instructions for tasks to be performed by the user during a first subset of the treatment period, wherein the tasks include one or more of prescribed blood glucose measurement pairs to be measured before and after meals, prescribed timing and dosage of medication to be consumed by the user, a prescribed amount of carbohydrates to be consumed by the user, or prescribed exercise for the user to perform, wherein the one or more machine learning algorithms include one or more of artificial neural networks, Bayesian statistics, case-based reason, decision trees, inductive logic processing, Gaussian process regression, Gene expression programming, Logistic model trees, stochastic modeling, or statistical modeling;

outputting the generated treatment plan, using the one or more processors, to the user via an electronic device of the user;

electronically receiving, using the one or more processors, data relating to the treatment plan during the first subset of the treatment period, the data relating to the treatment plan including types, timing, and dosages of medications consumed by the user, times and amounts of carbohydrates consumed by the user, amount of sleep of the user, amount of exercise performed by the user, and blood glucose levels of the user;

revising the treatment plan, using the one or more processors, for a subsequent subset of the treatment period based on determined medication compliance, determined diet compliance, determined exercise compliance, and identified patterns;

outputting the revised treatment plan to the user, using the one or more processors, via the electronic device, wherein the revised treatment plan includes one or more tasks to be performed by the user during the subsequent subset of the treatment period, wherein the tasks include a change in the one or more of the prescribed blood glucose measurement pairs to be measured before and after meals, the prescribed timing and dosage of medication to be consumed by the user, the prescribed amount of carbohydrates for the user to consume, or the prescribed exercise for the user to perform, as compared to the first subset of the treatment period;

determining, using the one or more processors, tendency of the user to follow at least one of a medication regimen, a diet regimen, and an exercise regimen, wherein the generating the treatment plan for the user to achieve the goal also is based on the determined tendency of the user to follow the medication regimen, the diet regimen, and the exercise regimen;

determining, using the one or more processors, based on the identified patterns, a trigger event that occurs before an adverse effect on the blood glucose levels of the user; and sending a notification to the user, using the one or more processors, via the electronic device of the user upon detecting a subsequent instance of the trigger event, wherein the notification includes an identification of the trigger event to the user and an identification of the adverse effect on the blood glucose levels that occur after the trigger event.

11. The system of claim 10, further including receiving an indication from the user that the user would like to exercise, and, after receiving the indication from the user, retrieving GPS data from the electronic device of the user, and generating a route for the user to walk along, wherein a distance of the route corresponds to the prescribed exercise to the user in the treatment plan.

12. The system of claim 10, further comprising determining a trend of the blood glucose values and further determining a range for an upcoming blood glucose value based on the trend and a bolus insulin delivery time.

13. The system of claim 10, wherein the cohort data is generated based on one or more individuals having one or more similarities with the user, the one or more similarities comprising a physical condition, a medical condition, and a psycho-determinant condition.

14. The system of claim 10, wherein the cohort data is generated based on one or more individuals that match a demographic of the user.

15. The system of claim 14, wherein the demographic is one or more of an ethnicity, a gender, an age range, a height, and a weight.

16. The system of claim 14, wherein the cohort data is based on the one or more individuals each having a successful treatment plan for a medical condition shared by the user and the one or more individuals.

17. The system of claim 10, wherein the treatment plan for the user to achieve the goal is further based on length of time that the user has been diagnosed with the blood glucose condition.

18. A computer-implemented method for managing blood glucose levels of a user, the method comprising:
- electronically receiving at a server, using one or more processors, before generation of a treatment plan, data, including types and dosages of medications consumed by the user, and A1C values of the user;
- storing, using the one or more processors, the received data in a database connected to the one or more processors;
- extracting metadata, using the one or more processors, from the stored data;
- inputting, using the one or more processors, the metadata into one or more machine learning algorithms to generate (a) a goal for the user and wherein the machine learning algorithms generate the goal based at least on cohort data for a cohort associated with the user and (b) the treatment plan for the user to achieve the goal based on a length of time that the user has been diagnosed with a blood glucose condition, and the types and dosages of medications consumed by the user, wherein the treatment plan includes instructions for tasks to be performed by the user during a first subset of a treatment period, wherein the tasks include one or more of prescribed blood glucose measurement pairs to be measured before and after meals, prescribed timing and dosage of medication to be consumed by the user, a prescribed amount of carbohydrates to be consumed by the user, or prescribed exercise for the user to perform, wherein the one or more machine learning algorithms include one or more of artificial neural networks, Bayesian statistics, case-based reason, decision trees, inductive logic processing, Gaussian process regression, Gene expression programming, Logistic model trees, stochastic modeling, or statistical modeling; outputting the generated treatment plan, using the one or more processors, to the user via an electronic device of the user;
- electronically receiving, using the one or more processors, data relating to the treatment plan during the first subset of the treatment period, the data relating to the treatment plan including types, timing, and dosages of medications consumed by the user, times and amounts of carbohydrates consumed by the user, and blood glucose levels of the user;
- outputting a revised treatment plan to the user, using the one or more processors, via the electronic device, wherein the revised treatment plan includes one or more tasks to be performed by the user during a subsequent subset of the treatment period, wherein the tasks include a change in the one or more of the prescribed blood glucose measurement pairs to be measured before and after meals, the prescribed timing and dosage of medication to be consumed by the user, the prescribed amount of carbohydrates for the user to consume, as compared to the first subset of the treatment period;
- receiving, using the one or more processors, global positioning system (GPS) data from the electronic device of the user;
- receiving an indication from the user that the user would like to exercise, and, after receiving the indication from the user, retrieving GPS data from the electronic device of the user, and generating a route for the user to walk along, wherein a distance of the route corresponds to the prescribed exercise to the user in the treatment plan;
- administering, via a software application downloaded to the electronic device of the user, and using the one or more processors, a questionnaire to the user;
- electronically receiving, using the one or more processors, user answers to the questionnaire;
- determining, using the one or more processors, based on the received user answers to the questionnaire, a tendency of the user to follow a medication regimen, and a diet regimen, wherein the generating the treatment plan for the user to achieve the goal also is based on the determined tendency of the user to follow the medication regimen, and the diet regimen;
- determining, using the one or more processors, a trigger event that occurs before an adverse effect on the blood glucose levels of the user; and
- sending a notification to the user, using the one or more processors, via the electronic device of the user upon detecting a subsequent instance of the trigger event, wherein the notification includes an identification of the trigger event to the user and an identification of the adverse effect on the blood glucose levels that occur after the trigger event, the trigger event is a day of the week, and the adverse effect on the blood glucose levels includes hyperglycemia.

19. The method of claim 18, wherein the goal includes a reduction in the A1C value of the user at an end of a treatment period, as compared to the A1C value of the user at a beginning of the treatment period.

20. The method of claim 18, wherein electronically receiving the data relating to the treatment plan during the first subset of the treatment period further comprises receiving an amount of sleep of the user.

* * * * *

UNITED STATES PATENT AND TRADEMARK OFFICE
CERTIFICATE OF CORRECTION

| | |
|---|---|
| PATENT NO. | : 11,587,681 B2 |
| APPLICATION NO. | : 17/192433 |
| DATED | : February 21, 2023 |
| INVENTOR(S) | : Kevin McRaith et al. |

It is certified that error appears in the above-identified patent and that said Letters Patent is hereby corrected as shown below:

On the Title Page

Column 1, in reference to the first inventor listed in Item (72), delete "Nonth Potomac" and insert --North Potomac--.

In the Claims

On Column 37, Line 12, Claim 8, delete "to the" and insert --to--.

Signed and Sealed this
Eighteenth Day of April, 2023

*Katherine Kelly Vidal*

Katherine Kelly Vidal
*Director of the United States Patent and Trademark Office*